US006668194B2

(12) United States Patent
VanHout

(10) Patent No.: US 6,668,194 B2
(45) Date of Patent: Dec. 23, 2003

(54) METHOD AND APPARATUS FOR MONITORING CONDUCTION TIMES IN A BI-CHAMBER PACING SYSTEM

(75) Inventor: Warren L. VanHout, Saline, MI (US)

(73) Assignee: Medtronic, Inc., Minneapolis, MN (US)

( * ) Notice: Subject to any disclaimer, the term of this patent is extended or adjusted under 35 U.S.C. 154(b) by 200 days.

(21) Appl. No.: 09/906,508

(22) Filed: Jul. 16, 2001

(65) Prior Publication Data

US 2003/0014084 A1 Jan. 16, 2003

(51) Int. Cl.[7] .............................................. A61N 1/362
(52) U.S. Cl. ............................................. 607/9; 607/17
(58) Field of Search .............................. 607/9, 15, 17, 607/18, 25

(56) References Cited

U.S. PATENT DOCUMENTS

| | | | |
|---|---|---|---|
| 3,937,226 A | 2/1976 | Funke | 607/14 |
| 4,088,140 A | 5/1978 | Rockland et al. | 607/14 |
| 4,332,259 A | 6/1982 | McCorkle, Jr. | 607/123 |
| 4,354,497 A | 10/1982 | Kahn | 607/5 |
| 4,428,378 A | 1/1984 | Anderson et al. | 607/19 |
| 4,458,677 A | 7/1984 | MrCorkle, Jr. | 607/123 |
| 4,548,203 A | 10/1985 | Tacker, Jr. et al. | 607/27 |
| 4,928,688 A | 5/1990 | Mower | 607/9 |
| 4,972,834 A | 11/1990 | Begemann et al. | 607/25 |
| 5,052,388 A | 10/1991 | Sivula et al. | 607/22 |
| 5,174,289 A | 12/1992 | Cohen | 607/9 |
| 5,267,560 A | 12/1993 | Cohen | 607/25 |
| 5,403,356 A | 4/1995 | Hill et al. | 607/14 |
| 5,514,161 A | 5/1996 | Limousin | 607/9 |
| 5,584,867 A | 12/1996 | Limousin et al. | 607/9 |
| 5,674,259 A | 10/1997 | Gray | 607/20 |
| 5,720,768 A | 2/1998 | Verboven-Nelissen | 607/9 |
| 5,792,203 A | 8/1998 | Schroeppel | 607/30 |
| 5,797,970 A | 8/1998 | Pouvreau | 607/9 |
| 5,902,324 A | 5/1999 | Thompson et al. | 607/9 |
| 6,129,744 A | 10/2000 | Boute | 607/25 |
| 6,219,579 B1 * | 4/2001 | Bakels et al. | 607/17 |
| 6,456,878 B1 * | 9/2002 | Yerich et al. | 607/9 |
| 6,473,645 B1 * | 10/2002 | Levine | 607/9 |
| 6,477,415 B1 * | 11/2002 | Yerich et al. | 607/9 |
| 2001/0012953 A1 * | 8/2001 | Molin et al. | |

OTHER PUBLICATIONS

Daubert et al., "Permanent Dual Atrium Pacing in Major Intra-atrial Conduction Blocks: A Four Years Experience", PACE (vol. 16, Part II, NASPE Abstract 141, p.885, Apr. 1993).

Daubert et al., "Permanent Left Ventricular Pacing With Transvenous Leads Inserted Into The Coronary Veins", PACE (vol. 21, Part II, pp. 239–245, Jan. 1998).

Cazeau et al., "Four Chamber Pacing in Dilated Cardiomyopathy", PACE (vol. 17, Part II, pp. 1974–1979, Nov. 1994).

Daubert et al., "Renewal of Permanent Left Atrial Pacing via the Coronary Sinus", PACE (vol. 15, Part II, NASPE Abstract 255, p. 572, Apr. 1992).

* cited by examiner

Primary Examiner—Carl Layno
(74) Attorney, Agent, or Firm—Girma Wolde-Michael; Michael C. Soldner

(57) ABSTRACT

A method and apparatus for deriving trend data indicative of the state of heart failure in a cardiac pacing system capable of delivering electrical stimulus to first and second ventricular sites that includes a timing circuit to begin measuring a time interval from a first ventricular event occurring at a selected one of the first and second ventricular sites, a sensing circuit coupled to the timing circuit to detect a second ventricular depolarization in the other of the first and second ventricular sites, and a storage device coupled to the timing circuit to store one or more elapsed conduction times that may be utilized as an indicator of the state of heart failure.

65 Claims, 10 Drawing Sheets

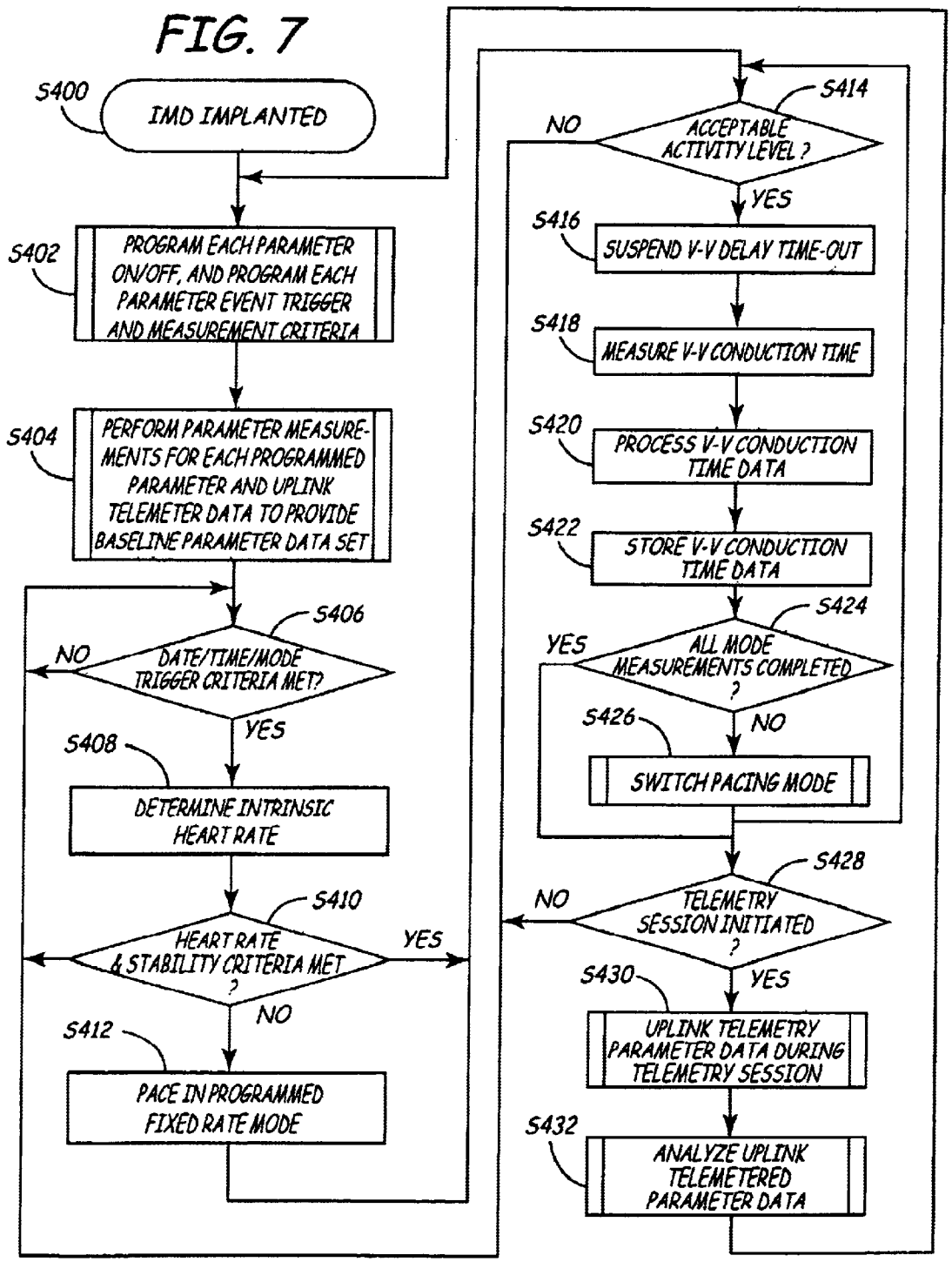

METHOD AND APPARATUS FOR MONITORING CONDUCTION TIMES IN A BI-CHAMBER PACING SYSTEM

FIELD OF THE INVENTION

The present invention pertains to cardiac pacing systems that pace and sense in at least a first site in the heart and sense conducted electrical signals at a second site in the heart and measuring and accumulating electrical conduction times between the first and second sites to derive trend data indicative of the state of heart failure.

BACKGROUND OF THE INVENTION

CHF is defined generally as the inability of the heart to deliver enough blood, i.e., to supply sufficient cardiac output, to the peripheral tissues to meet metabolic demands. Frequently CHF is manifested by left ventricular dysfunction (LVD), but it can have a variety of sources. For example, CHF patients may have any one of several different conduction defects. The natural electrical activation system through the heart involves sequential events starting with the sino-atrial (SA) node, and continuing through the atrial conduction pathways of Bachmann's bundle and internodal tracts at the atrial level, followed by the atrio-ventricular (AV) node, Common Bundle of His, right and left bundle branches, and final distribution to the distal myocardial terminals via the Purkinje fiber network. A common type of intra-atrial conduction defect is known as intra-atrial block (IAB), a condition where the atrial activation is delayed in getting from the right atrium (RA) to the left atrium (LA). In left bundle branch block (LBBB) and right bundle branch block (RBBB), the activation signals are not conducted in a normal fashion along the right or left bundle branches respectively. Thus, in a patient with bundle branch block, the activation of the right ventricle (RV) and the left ventricle (LV) is slowed, and the QRS is seen to widen due to the increased time for the activation to traverse the conduction path. For example, in a patient with LBBB, the delay in the excitation from the RV to the LV can be as high as 120 to 150 ms.

Thus, cardiac depolarizations that naturally occur in one upper or lower heart chamber are not conducted in a timely fashion either within the heart chamber or to the other upper or lower heart chamber diseased hearts exhibiting LVD and CHF. In such cases, the right and left heart chambers do not contract in optimum synchrony with each other, and cardiac output suffers due to the conduction defects. In addition, spontaneous depolarizations of the LA or LV occur at ectopic foci in these left heart chambers, and the natural activation sequence is grossly disturbed. In such cases, cardiac output deteriorates because the contractions of the right and left heart chambers are not synchronized sufficiently to eject blood therefrom. Furthermore, significant conduction disturbances between the RA and LA can result in left atrial flutter or fibrillation.

More particularly, as described in commonly assigned U.S. Pat. No. 6,129,744, LVD and other forms of heart failure are manifested by reduced ejection fraction from the LV thereby reducing stroke volume and promoting pulmonary edema limiting the patient's ability to exercise. Patients suffering from LVD are also known to have elevated levels of catecholamines at rest because the body is attempting to increase cardiac output that induce a higher resting heart rate. In addition, the QT interval for such a patient is affected by the catecholamine level and thus has a changed pattern during exercise as well. These patients have a decreased QT response, or smaller change in QT, during exercise, such that the QT interval shortening during exercise is smaller than that found normally. Although QT interval is influenced independently by heart rate alone, as well as by exercise and catecholemines, it is not known to what extent each of these factors or both are responsible for the changed QT response to exercise in LVD patients. However, it is known that patients suffering LVD clearly have a different pattern of QT interval shortening during exercise. Moreover, the changed conductive patterns or a heart in heart failure are manifested by other changes in the PQRST waveforms, particularly an abnormally wide or long duration of the ventricular depolarization signal, or QRS.

It has been proposed that various conduction disturbances involving both bradycardia and tachycardia of a heart chamber could benefit from pacing pulses applied at multiple pace/sense electrode sites positioned in or about a single heart chamber or in the right and left heart chambers in synchrony with a depolarization which has been sensed at least one of the pace/sense electrode sites. It is believed that atrial and left ventricular cardiac output can be significantly improved when left and right chamber synchrony is restored, particularly in patients suffering from dilated cardiomyopathy, LVD and CHF.

A number of proposals have been advanced for providing pacing therapies to alleviate heart failure conditions and restore synchronous depolarization and contraction of a single heart chamber or right and left, upper and lower, heart chambers as described in detail in the above referenced '744 patent and in commonly assigned U.S. Pat. Nos. 5,403,356, 5,797,970 and 5,902,324 and in U.S. Pat. Nos. 5,720,768 and 5,792,203. The proposals appearing in U.S. Pat. Nos. 3,937,226, 4,088,140, 4,548,203, 4,458,677, 4,332,259 are summarized in U.S. Pat. Nos. 4,928,688 and 5,674,259. The advantages of providing sensing at pace/sense electrodes located in both the right and left heart chambers is addressed in the '688 and '259 patents, as well as in U.S. Pat. Nos. 4,354,497, 5,174,289, 5,267,560, 5,514,161, and 5,584,867.

The medical literature also discloses a number of approaches of providing bi-atrial and/or bi-ventricular pacing as set forth in: Daubert et al., "Permanent Dual Atrium Pacing in Major Intra-atrial Conduction Blocks: A Four Years Experience", *PACE* (Vol. 16, Part II, NASPE Abstract 141, p.885, April 1993); Daubert et al., "Permanent Left Ventricular Pacing With Transvenous Leads Inserted Into The Coronary Veins", *PACE* (Vol. 21, Part II, pp. 239–245, January 1998); Cazeau et al., "Four Chamber Pacing in Dilated Cardiomyopathy", *PACE* (Vol. 17, Part II, pp. 1974–1979, November 1994); and Daubert et al., "Renewal of Permanent Left Atrial Pacing via the Coronary Sinus", *PACE* (Vol. 15, Part II, NASPE Abstract 255, p. 572, April 1992).

In the above-referenced '324 patent, an AV synchronous pacing system is disclosed providing three or four heart chamber pacing through pace/sense electrodes located in or adjacent one or both of the RA and LA and in or adjacent to the RV and LV. During an AV delay and during a V-A escape interval, a non-refractory ventricular sense event detected at either the RV or LV pace/sense electrodes starts a conduction time window (CDW) timer. A ventricular pace pulse is delivered to the other of the LV or RV pace/sense electrodes at the time-out of the CDW if a ventricular sense event is not detected at that site while the CDW times out.

The above-referenced '744 patent discloses a rate responsive, bi-ventricular pacemaker having one or more sensors for sensing a parameter indicative of the physiologic need for cardiac output, and for pacing the patient on demand between a lower rate limit (LRL) and an upper rate limit (URL). In a specific embodiment, the pacemaker determines QT interval, and stores data representative of changes in QT interval as a function of paced heart rate and/or the patient's spontaneous lower rate when at rest. Variations in the correlation of QT interval and heart rate, and/or variations in patient lower rate at rest are processed to provide a time trend, or profile, from which a determination is made as to whether or not LVD is indicated. In alternate embodiments, other data derived from cardiac signals is processed and stored, e.g., QRS width, T-wave amplitude, etc. A change in the variation of T-wave amplitude with respect to exercise, and consequent heart rate, can be easily measured and tracked in a QT rate responsive pacemaker, or any pacemaker adapted to sense and recover the T-waves. Likewise, as noted above, changes in QRS duration (width) and/or morphology may also be detected and tracked for detection of a trend. Trends in this data are periodically evaluated, e.g., on a daily basis, and stored for downloading to an external programmer for deriving an indication of LVD, or onset or progression of LVD or for automatic initiation of a treatment response signals.

An algorithm for automatically adjusting the rate responsive parameters, i.e., the correlation function between QT and desired rate is suitably performed on a daily basis. The pacemaker measures a slope of the correlation function at the LRL, and adjusts the QT-rate function between LRL and URL accordingly as disclosed in commonly assigned U.S. Pat. No. 4,972,834. If such changes are stored and analyzed for a trend, progress toward LVD can be indicated. Likewise, if it is found that the patient heart rate is not dropped to the programmed LRL during nighttime, such that the spontaneous lower rate has had an upward progression, this trend can also be used as an indicator of the onset of LVD.

As asserted in the '744 patent, these functions can be performed in an implanted monitor solely dedicated to detection and storage of cardiac data and processing of such data to provide an indication of LVD when interrogated. In a more preferred embodiment, a rate responsive pacemaker system is disclosed that can pace and sense in any combination or all of the four cardiac chambers. The treatment response upon an indication of onset of LVD has a number of embodiments, including changing the rate response function; changing physiologic sensor blending for dual or plural sensor rate responsive pacemakers; initiating three or four chamber pacing to achieve improved left heart response, e.g., synchronous ventricular pacing and/or other multi-chamber sequential pacing; and providing for a measured release of an appropriate drug for treating the LVD. In yet another disclosed embodiment, the pacemaker is implanted with software for carrying out normal dual chamber pacing, but the software can be upgraded by programmer downloading to provide different pacing functions, or to function as a three or four chamber pacemaker, along with utilization of an additional lead or leads for delivering stimulus pulses to the left heart chambers.

Chronically collected data from patients with heart failure is needed so that the treating cardiologist can properly and accurately chart the progression, determine the nature of the heart failure, and be able to implement the optimal treatment in a timely fashion. There is a substantial need in the art for a pacemaker or other implanted device having the capacity to identify the progression or remission of heart failure and to provide such indication to the patient's physician so that options can be assessed from time to time to treat the changing patient condition.

SUMMARY OF THE INVENTION

In view of the above need, the present invention provides a system and method for monitoring patient cardiac signals and processing such signals within an implantable medical device (IMD) to provide data from which the onset or progression of heart failure can be determined. It is to be understood that the invention is applicable to various forms of heart failure, including left heart conduction disorders such as IAB, LBBB and RBBB, and other forms of heart dysfunction including LVD.

The present invention is implemented in a wide variety of ways. In the broadest context, the present invention pertains to cardiac pacing systems that pace and sense in at least a first site in the heart and sense conducted electrical signals at a second site in the heart and measuring and accumulating electrical conduction times between the first and second sites to derive trend data indicative of the state of heart failure. The present invention is preferably embodied in a multi-site, cardiac pacing system having memory for storing such conduction time data.

The first and second sites can be separated sites in a single heart chamber of right heart chamber (RHC) and left heart chamber (LHC) sites, e.g., right and left atrial (RA and LA) sites or right and left ventricular (RV and LV) sites. In a conduction measurement operating mode, one or both of the RHC-LHC and LHC-RHC conduction times are measured and conduction time data is stored in memory along with a date and time stamp and any other data of interest. A series of RHC-LHC and LHC-RHC conduction times can be measured and processed to determine maximum, minimum and average RHC-LHC and LHC-RHC conduction times that are stored in memory.

The RHC-LHC and LHC-RHC conduction time measurements can be made from intrinsic sense events at the first RHC or LHC site to an intrinsic sense event at the second LHC and RHC, respectively, site. Preferably, the first site is paced at the time-out of a pacing escape interval or upon a sense event. In this way an RHP-LHC conduction time is measured from an RHC pace (RHP) pulse to an LHC sense (LHS) event and an LHP-RHC conduction time is measured from an LHC pace (LHP) pulse to an RHC sense (RHS) event. The RHP-LHC conduction time can be compared with the LHP-RHC conduction time in the assessment of the heart failure state.

In one preferred embodiment, a multi-site, cardiac pacing system is provided wherein ventricular pacing pulses are delivered to first and second ventricular sites synchronously within a V-V pace delay at a predetermined pacing rate in accordance with the steps of and means for: (a) timing a ventricular pacing escape interval; (b) detecting a ventricular depolarization in a selected one of the first and second ventricular sites within the pacing escape interval and, in response, terminating the pacing escape interval and providing a first ventricular sense (VS) event; (c) delivering a first ventricular pace (VP) pulse to the selected one of the first and second ventricular sites upon either the time-out of the pacing escape interval without provision of a first VS event or upon provision of the first VS event during time-out of the pacing escape interval; (d) timing the V-V pace delay from a first VS event occurring prior to the time-out of the pacing escape interval or from a first VP pulse delivered either upon provision of the first VS event or upon time-out of the pacing escape interval; and (e) delivering a second VP pulse to the other of the first and second ventricular sites upon the time-out of the V-V pace delay.

In accordance with the present invention, an interventricular V-V conduction time measurement mode is entered periodically to measure the V-V conduction time between the first and second ventricular sites. Steps (d) and (e) can be suspended or the measurement can take place when there is a V-V conduction time that is shorter than the prevailing V-V pace delay. The V-V conduction time is measured from a VS event or VP pulse delivered to the selected one of the first and second ventricular sites to the VS event at the other one of the first and second ventricular sites, and the measured V-V conduction time is stored in memory. The measured V-V conduction time can be one or more of a VS-VS conduction time, a VP-VS conduction time and a VS/VP-VS conduction time. In each case, a single data point measured V-V conduction time may be obtained and stored or the high and low measured V-V conduction times and an average V-V conduction time can be obtained from a series of measured V-V conduction times. The measured V-V conduction time (or times if more than one mode is entered) as well as related data including a date and time stamp of the measurement event, the prevailing heart rate, and the activity level of the patient or other indicator of physiologic need for cardiac output are stored in IMD memory for subsequent analysis. Trend data evidencing any change in the intrinsic conduction time between the first and second ventricular sites gathered over a period of days, weeks and months provides a valuable indication as to whether the heart failure state is improving, worsening or staying about the same.

More particularly, a method and apparatus is provided that periodically derives trend data representative of the state of heart failure as evidenced by the V-V conduction time between the first and second ventricular sites by the steps of or means for: (f) suspending steps (d) and (e) while steps (a) through (c) are performed for one or more heart cycle; (g) detecting a ventricular depolarization in the other of the first and second ventricular sites during the one or more heart cycle and providing a second VS event in response; and (g) measuring and storing in memory one of the elapsed VS-VS conduction time from a first VS event or the elapsed VP-VS conduction time from the first VP pulse delivered at the end of the pacing escape interval or the elapsed VS/VP-VS conduction time from the first VP pulse delivered upon a first VS event occurring during the time-out of the pacing escape interval, whereby trend data representative of the state of heart failure as evidenced by changes in the stored one of the elapsed VS-VS conduction time, the VP-VS conduction time, and the VS/VP-VS conduction time between the first and second ventricular sites is accumulated for analysis of the trend.

The present invention is preferably embodied in a multi-site, AV sequential, cardiac pacing system wherein ventricular pacing pulses are delivered to the right and left ventricles synchronously within a V-V pace delay following time-out of an AV delay from a preceding delivered atrial pace pulse or an atrial sense event and operating in accordance with the steps of: (a) timing an AV delay from a preceding delivered atrial pace pulse or an atrial sense event; (b) detecting a ventricular depolarization at one of a first and second ventricular site within the AV delay and, in response, terminating the AV delay and providing a ventricular sense event; (c) delivering a ventricular pace pulse to a selected one of the first and second ventricular sites upon the time-out of the AV delay; (d) timing the V-V pace delay from a ventricular sense event occurring prior to the time-out of the AV delay or from a ventricular pace pulse delivered at the end of the AV delay; and (e) delivering a ventricular pace pulse to the other of the first and second ventricular sites upon the time-out of the V-V pace delay.

In one variation, the conduction time measurement mode causes the triggered pacing mode to be entered wherein step (b) is modified by delivering a VP pulse to the selected one of the first and second ventricular sites upon the a VS occurring during the time-out of the AV delay or during the V-A escape interval, steps (d) and (e) are suspended, and a measurement of the intrinsic VP-VS conduction time elapsing from the delivery of the ventricular pace pulse to the selected one of the first and second ventricular sites and the detection of the conducted depolarization in the other of the first and second ventricular sites is made and stored in memory.

In a further variation, the triggered pacing mode is not entered, and the intrinsic ventricular rate examined to ensure that it is above the programmed LRL such that the ventricular depolarization consistently falls within the prevailing AV delay and inhibits delivery of a ventricular pacing pulse at the timeout of the AV delay. Steps (d) and (e) are suspended, the elapsed VS-VS conduction time between the sensed ventricular depolarization at one of the first and second ventricular sites and the subsequent ventricular depolarization at the other one of the first and second ventricular sites is measured, and the elapsed VS-VS conduction time is stored in memory.

In a still further variation, an overdrive pacing mode is entered that synchronously paces the atrial chamber and the selected one of the first and second ventricular sites at a rate exceeding the prevailing intrinsic heart rate to ensure capture. Steps (d) and (e) are suspended, and a measurement of the intrinsic VP-VS conduction time elapsing from the delivery of the ventricular pace pulse to the selected one of the first and second ventricular sites and the detection of the conducted depolarization in the other of the first and second ventricular sites is made and stored in memory. Optionally, only the selected ones of the first and second ventricular sites could be paced at the overdrive pacing rate.

The first and second ventricular sites preferably comprise RV and LV pace/sense electrode sites, and RV event and LV event signals are sensed at the RV and LV pace/sense electrodes. Preferably, the selected one of the RV and LV that a ventricular pace pulse is delivered to is the RV, and the ventricular depolarization is sensed in the LV to determine a VS/VP-VS or VP-VS RV-LV conduction time. However, in each of the above embodiments, the measurement operating mode can be repeated to deliver a ventricular pace pulse is to the LV, and the ventricular depolarization is sensed in the RV to determine a VS/VP-VS or VP-VS LV-RV conduction time.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIG. 7 is a flow chart illustrating the steps of periodically measuring and storing the V-V conduction time and telemetering the stored V-V conduction time data to an external programmer;

DETAILED DESCRIPTION OF THE PREFERRED EMBODIMENTS

In the following detailed description, references are made to illustrative embodiments for carrying out the invention. It is understood that other embodiments may be utilized without departing from the scope of the invention. For example, the invention is disclosed in detail in FIGS. 2 and 3 in the context of an AV sequential, bi-ventricular, pacing system operating in demand, atrial tracking, and triggered pacing modes in accordance with FIGS. 4 through 6A–6B for restoring synchrony in depolarizations and contraction of left and right ventricles in synchronization with atrial sensed and paced events for treating bradycardia in those chambers. This embodiment of the invention is programmable to operate as a three or four chamber pacing system having an AV synchronous operating mode for restoring upper and lower heart chamber synchronization and right and left atrial and/or ventricular chamber depolarization synchrony. Of course, the present invention may also be practiced in a simpler, three-chamber pacing system eliminating certain of the features of the preferred embodiment described herein.

It should be appreciated that the present invention may be utilized particularly to treat patients suffering various forms of heart failure and bradycardia. The pacing system of the present invention can also be incorporated into an antitachyarrhythmia system including specific high rate pacing and cardioversion shock therapies for providing staged therapies to treat a diagnosed tachyarrhythmia.

Moreover, the present invention can implemented simply in a multi-site ventricular demand pacing system where ventricular pacing and sensing are conducted at least at two ventricular sites in the same ventricle or having at least one site in the RV and another site in the LV and measuring the V-V conduction times between the sites. Similarly, the present invention can implemented simply in a multi-site atrial demand pacing system where atrial pacing and sensing are conducted at least at two atrial sites in the same atrial chamber or having at least one site in the RA and another site in the LA and measuring the A-A conduction times between the sites. Such systems and methods are described in reference to FIG. 9.

Figure 1:
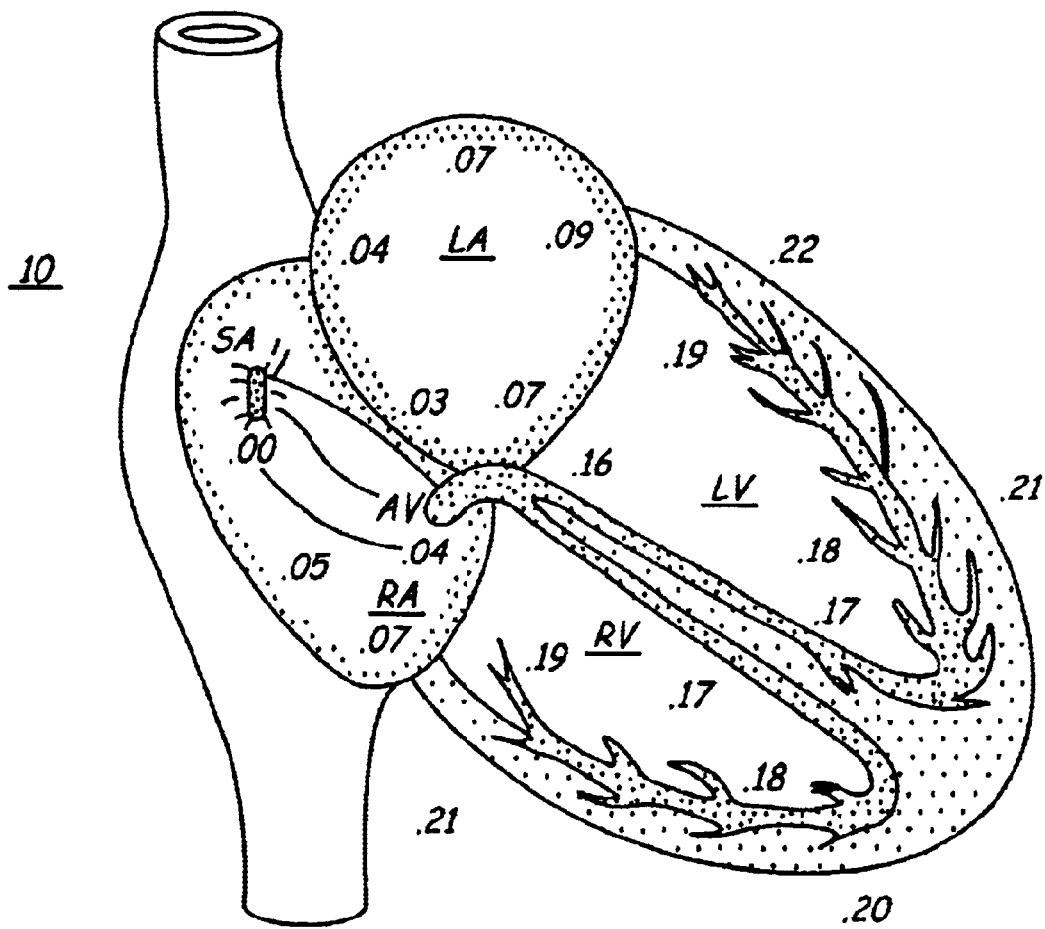
FIG. 1 is an illustration of transmission of the cardiac depolarization waves through the heart in a normal electrical activation sequence.

In FIG. 1, heart 10 includes the upper heart chambers, the right atrium (RA) and left atrium (LA), and the lower heart chambers, the right ventricle (RV) and left ventricle (LV) and the coronary sinus (CS) extending from the opening in the right atrium laterally around the atria to form the great vein (GV) that extends further inferiorly into branches of the GV. FIG. 1 is an illustration of transmission of the cardiac depolarization waves through the RA, LA, RV and LV in a normal electrical activation sequence at a normal heart rate with the conduction times exhibited thereon in seconds. The cardiac cycle commences normally with the generation of the depolarization impulse at the SA Node in the right atrial wall and its transmission through the atrial conduction pathways of Bachmann's Bundle and the Internodal Tracts at the atrial level into the left atrial septum. The RA depolarization wave reaches the atrio-ventricular (AV) node and the atrial septum within about 40 msec and reaches the furthest walls of the RA and LA within about 70 msec, and the atria complete their contraction as a result. The aggregate RA and LA depolarization wave appears as the P-wave of the PQRST complex when sensed across external ECG electrodes and displayed. The component of the atrial depolarization wave passing between a pair of unipolar or bipolar pace/sense electrodes, respectively, located on or adjacent the RA or LA is also referred to as a sensed P-wave. Although the location and spacing of the external ECG electrodes or implanted unipolar atrial pace/sense electrodes has some influence, the normal P-wave width does not exceed 80 msec in width as measured by a high impedance sense amplifier coupled with such electrodes. A normal near field P-wave sensed between closely spaced bipolar pace/sense electrodes and located in or adjacent the RA or the LA has a width of no more than 60 msec as measured by a high impedance sense amplifier.

The depolarization impulse that reaches the AV Node is distributed inferiorly down the bundle of His in the intra-ventricular septum after a delay of about 120 msec. The depolarization wave reaches the apical region of the heart about 20 msec later and then travels superiorly though the Purkinje Fiber network over the remaining 40 msec. The aggregate RV and LV depolarization wave and the subsequent T-wave accompanying re-polarization of the depolarized myocardium are referred to as the QRST portion of the PQRST cardiac cycle complex when sensed across external ECG electrodes and displayed. When the amplitude of the QRS ventricular depolarization wave passing between a bipolar or unipolar pace/sense electrode pair located on or adjacent the RV or LV exceeds a threshold amplitude, it is detected as a sensed R-wave. Although the location and spacing of the external ECG electrodes or implanted unipolar ventricular pace/sense electrodes has some influence, the normal R-wave width does not exceed 80 msec in width as measured by a high impedance sense amplifier. A normal near field R-wave sensed between closely spaced bipolar pace/sense electrodes and located in or adjacent the RV or the LV has a width of no more than 60 msec as measured by a high impedance sense amplifier.

The typical normal conduction ranges of sequential activation are also described in the article by Durrer et al., entitled "Total Excitation of the Isolated Human Heart", in CIRCULATION (Vol. XLI, pp. 899–912, June 1970). This normal electrical activation sequence becomes highly disrupted in patients suffering from advanced CHF and exhibiting intra-atrial cardiac dysfunction (IACD), LBBB, RBBB, and/or intra-ventricular cardiac dysfunction (IVCD). These conduction defects exhibit great asynchrony between the RV and the LV due to conduction disorders along the Bundle of His, the Right and Left Bundle Branches or at the more distal Purkinje Terminals. Typical intra-ventricular peak-peak asynchrony can range from 80 to 200 msec or longer. In RBBB and LBBB patients, the QRS complex is widened far beyond the normal range to from >120 msec to 250 msec as measured on surface ECG. This increased width demonstrates the lack of synchrony of the right and left ventricular depolarizations and contractions.

In accordance with an aspect of the present invention, a method and apparatus is provided to restore the depolarization sequence of FIG. 1 and the synchrony between the right and left ventricular heart chambers that contributes to adequate cardiac output related to the optimal RV-LV conduction time. This restoration is effected through providing optimally timed cardiac pace pulses to the right and left ventricles as necessary and to account for the particular implantation sites of the pace/sense electrodes in relation to each heart chamber while maintaining AV synchrony. The present invention efficiently provides pacing at multiple ventricular pacing sites in a triggered pacing mode in response to a ventricular sense event detected at either ventricular pace/sense electrode site during the AV delay only.

Figure 2:
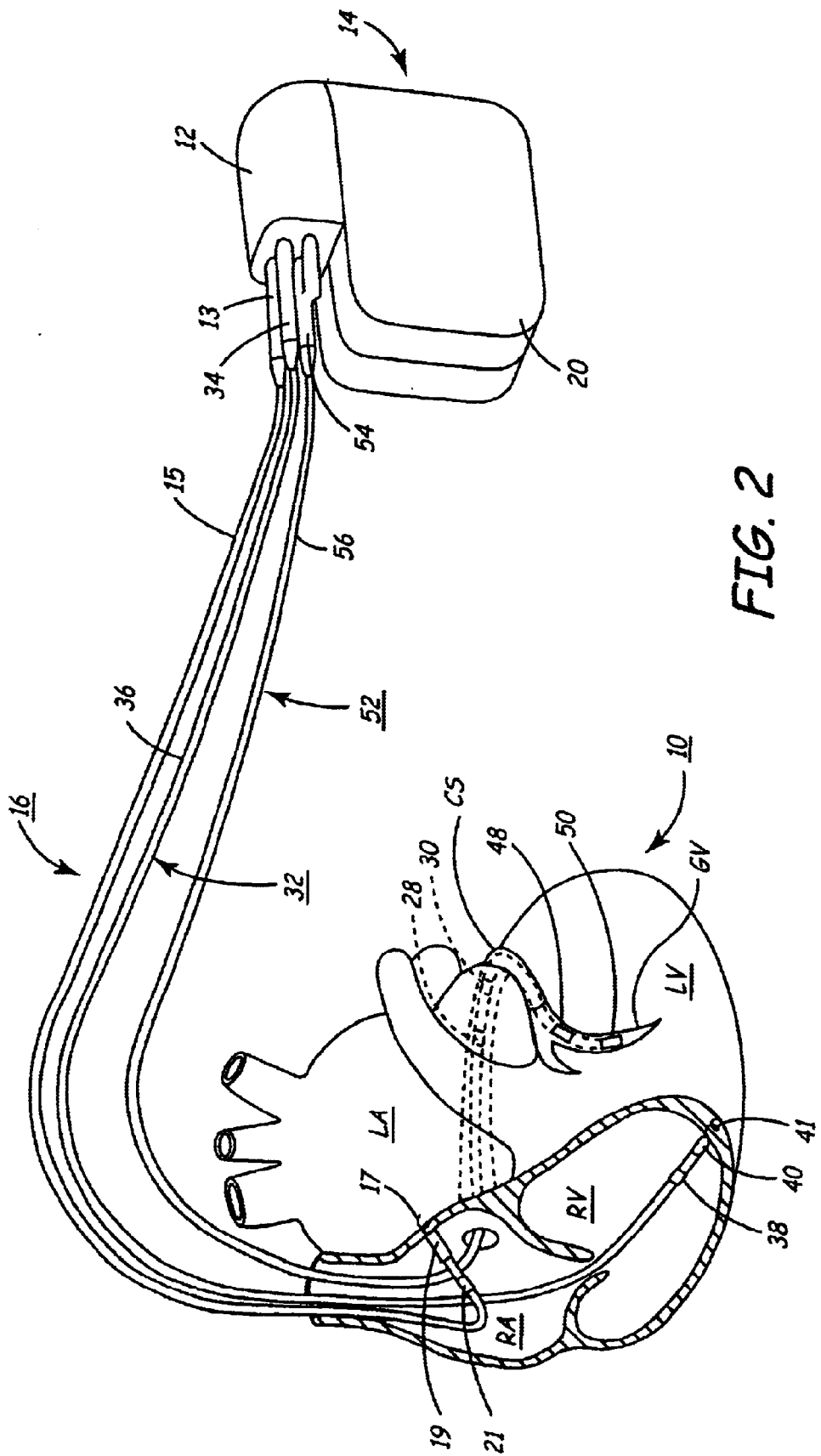
FIG. 2 is a schematic diagram depicting a four channel, bi-atrial and bi-ventricular, pacing system in which the present invention is preferably implemented.

FIG. 2 is a schematic representation of an implanted, three chamber cardiac pacemaker of the above noted types for restoring AV synchronous contractions of the atrial and ventricular chambers and simultaneous or sequential pacing of the right and left ventricles. The pacemaker IPG 14 is implanted subcutaneously in a patient's body between the skin and the ribs. Three endocardial leads 16, 32 and 52 connect the IPG 14 with the RA, the RV and the LV, respectively. Each lead has at least one electrical conductor and pace/sense electrode, and a remote indifferent can electrode 20 is formed as part of the outer surface of the housing of the IPG 14. As described further below, the pace/sense electrodes and the remote indifferent can electrode 20 (IND_CAN electrode) can be selectively employed to provide a number of unipolar and bipolar pace/sense electrode combinations for pacing and sensing functions, particularly sensing far field signals, e.g. a far field R-wave (FFRS). The depicted positions in or about the right and left heart chambers are also merely exemplary. Moreover other leads and pace/sense electrodes may be used instead of the depicted leads and pace/sense electrodes that are adapted to be placed at electrode sites on or in or relative to the RA, LA, RV and LV.

The depicted bipolar endocardial RA lead 16 is passed through a vein into the RA chamber of the heart 10, and the distal end of the RA lead 16 is attached to the RA wall by an attachment mechanism 17. The bipolar endocardial RA lead 16 is formed with an in-line connector 13 fitting into a bipolar bore of IPG connector block 12 that is coupled to a pair of electrically insulated conductors within lead body 15 and connected with distal tip RA pace/sense electrode 19 and proximal ring RA pace/sense electrode 21. Delivery of atrial pace pulses and sensing of atrial sense events is effected between the distal tip RA pace/sense electrode 19 and proximal ring RA pace/sense electrode 21, wherein the proximal ring RA pace/sense electrode 21 functions as an indifferent electrode (IND_RA). Alternatively, a unipolar endocardial RA lead could be substituted for the depicted bipolar endocardial RA lead 16 and be employed with the IND_CAN electrode 20. Or, one of the distal tip RA pace/sense electrode 19 and proximal ring RA pace/sense electrode 21 can be employed with the IND_CAN electrode 20 for unipolar pacing and/or sensing.

Bipolar, endocardial RV lead 32 is passed through the vein and the RA chamber of the heart 10 and into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38, wherein the proximal ring RV pace/sense electrode 38 functions as an indifferent electrode (IND_RV). Alternatively, a unipolar endocardial RV lead could be substituted for the depicted bipolar endocardial RV lead 32 and be employed with the IND_CAN electrode 20. Or, one of the distal tip RV pace/sense electrode 40 and proximal ring RV pace/sense electrode 38 can be employed with the IND_CAN electrode 20 for unipolar pacing and/or sensing.

In this illustrated embodiment, a bipolar, endocardial CS lead 52 is passed through a vein and the RA chamber of the heart 10, into the CS and then inferiorly in a branching vessel of the great vein GV to extend the proximal and distal LV CS pace/sense electrodes 48 and 50 alongside the LV chamber. The distal end of such a CS lead is advanced through the superior vena cava, the right atrium, the ostium of the coronary sinus, the coronary sinus (CS), and into a coronary vein descending from the coronary sinus, such as the great vein (GV).

In a four chamber or channel embodiment, LV CS lead 52 could bear proximal LA CS pace/sense electrodes 28 and 30 positioned along the CS lead body to lie in the larger diameter CS adjacent the LA. Typically, LV CS leads and LA CS leads do not employ any fixation mechanism and instead rely on the close confinement within these vessels to maintain the pace/sense electrode or electrodes at a desired site. The LV CS lead 52 is formed with a multiple conductor lead body 56 coupled at the proximal end connector 54 fitting into a bore of IPG connector block 12. A small diameter lead body 56 is selected in order to lodge the distal LV CS pace/sense electrode 50 deeply in a vein branching inferiorly from the great vein GV.

In this case, the CS lead body 56 would encase four electrically insulated lead conductors extending proximally from the more proximal LA CS pace/sense electrode(s) and terminating in a dual bipolar connector 54. The LV CS lead body would be smaller between the LA CS pace/sense electrodes 28 and 30 and the LV CS pace/sense electrodes 48 and 50. It will be understood that LV CS lead 52 could bear a single LA CS pace/sense electrode 28 and/or a single LV CS pace/sense electrode 50 that are paired with the IND_CAN electrode 20 or the ring electrodes 21 and 38, respectively for pacing and sensing in the LA and LV, respectively.

Figure 3:
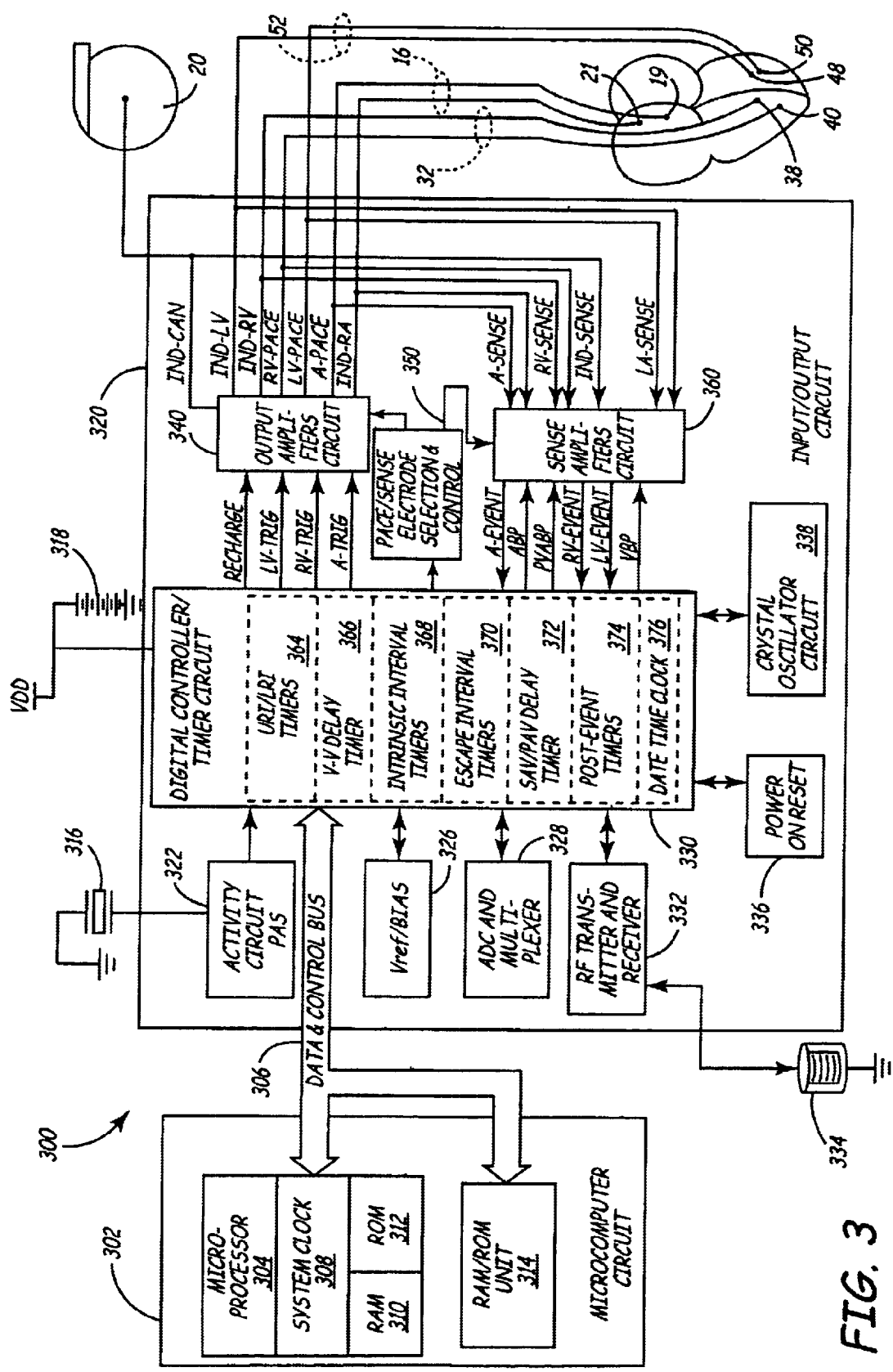
FIG. 3 is a simplified block diagram of one embodiment of IPG circuitry and associated leads employed in the system of FIG. 2 for providing four pacing channels that are selectively programmed in bi-atrial and/or bi-ventricular pacing modes.

In this regard, FIG. 3 depicts bipolar RA lead 16, bipolar RV lead 32, and bipolar LV CS lead 52 without the LA CS pace/sense electrodes 28 and 30 coupled with an exemplary IPG circuit 300 having programmable modes and parameters of a bi-ventricular DDDR type known in the pacing art. It will be understood that many other embodiments of the exemplary IPG circuit may be used within the context of the current embodiment.

The IPG circuit 300 is illustrated in a functional block diagram divided generally into a microcomputer circuit 302 and a pacing circuit 320. The pacing circuit 320 includes the digital controller/timer circuit 330, the output amplifiers circuit 340, the sense amplifiers circuit 360, the RF telemetry transceiver 332, the activity sensor circuit 322 as well as a number of other circuits and components described below.

Crystal oscillator circuit 338 provides the basic timing clock for the pacing circuit 320, while battery 318 provides power. Power-on-reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the pacing circuit 320, while analog to digital converter ADC and multiplexer circuit 328 digitizes analog signals and voltage to provide real time telemetry if a cardiac signals from sense amplifiers 360, for uplink transmission via transceiver 332. Voltage reference and bias circuit 326, ADC and multiplexer 328, power-on-reset circuit 336 and crystal oscillator circuit 338 may correspond to any of those presently used in current marketed implantable cardiac pacemakers.

If the IPG is programmed to a rate responsive mode, the signals output by one or more physiologic sensor are employed as a rate control parameter (RCP) to derive a physiologic escape interval. For example, the escape interval is adjusted proportionally the patient's activity level developed in the patient activity sensor (PAS) circuit 322 in the depicted, exemplary IPG circuit 300. The patient activity sensor 316 is coupled to the IPG housing and may take the form of a piezoelectric crystal transducer as is well known in the art. The output signal is processed and used as the RCP. Sensor 316 generates electrical signals in response to sensed physical activity that are processed by activity circuit 322 and provided to digital controller/timer circuit 330. Activity circuit 322 and associated sensor 316 may correspond to the circuitry disclosed in U.S. Pat. Nos. 5,052,388 and 4,428,378. Similarly, the present invention may be practiced in conjunction with alternate types of sensors such as oxygenation sensors, pressure sensors, pH sensors and respiration sensors, all well known for use in providing rate responsive pacing capabilities. Alternately, QT time may be used as the rate indicating parameter, in which case no extra sensor is required. Similarly, the present invention may also be practiced in non-rate responsive pacemakers.

Data transmission to and from the external programmer is accomplished by means of the telemetry antenna 334 and transceiver 332, which serves both to demodulate received downlink telemetry and to transmit uplink telemetry. Uplink telemetry capabilities will typically include the ability to transmit stored digital information such as operating modes and parameters, EGM histograms, and other events, as well as real time EGMs of atrial and/or ventricular electrical activity and Marker Channel pulses indicating the occurrence of sensed and paced depolarizations in the atrium and ventricle, as are well known in the pacing art.

Microcomputer 302 contains a microprocessor 304 and associated system clock 308 and on-processor RAM and ROM chips 310 and 312, respectively. In addition, microcomputer circuit 302 includes a separate RAM/ROM chip 314 to provide additional memory capacity. Microprocessor 304 normally operates in a reduced power consumption mode and is interrupt driven. Microprocessor 304 is awakened in response to defined interrupt events, which may include A-TRIG, RV-TRIG, and LV-TRIG signals generated by timers in digital timer/controller circuit 330, and/or A-EVENT, RV-EVENT, and LV-EVENT signals generated by sense amplifiers circuit 360, among others. The specific values of the intervals and delays timed by digital controller/timer circuit 330 are controlled by the microcomputer circuit 302 by means of data and control bus 306 from programmed-in parameter values and operating modes. In addition, if programmed to operate as a rate responsive pacemaker, a timed interrupt as may occur at predetermined time intervals may be provided in order to allow the microprocessor to analyze the activity sensor data and update the basic A-A, V-A or V-V escape interval. In addition, the microprocessor 304 may also serve to define variable AV delays and the bi-ventricular V-V pace delays from the activity sensor data.

In one embodiment of the invention, microprocessor 304 is a custom microprocessor adapted to fetch and execute instructions stored in RAM/ROM unit 314 in a conventional manner. It is contemplated, however, that other implementations may be suitable to practice the present invention. For example, an off-the-shelf, commercially-available microprocessor or microcontroller, or custom application-specific, hardwired logic, or state-machine type circuit may perform the functions of microprocessor 304.

Digital controller/timer circuit 330 operates under the general control of the microcomputer 302 to control timing and other functions within the pacing circuit 320 and includes a set of timing and associated logic circuits of which certain ones pertinent to the present invention are depicted. The depicted timing circuits include URI/LRI timers 364, V-V delay timer 366, intrinsic interval timers 368 for timing elapsed V-EVENT to V-EVENT intervals or V-EVENT to A-EVENT intervals or the V-V conduction interval, escape interval timers 370 for timing A-A, V-A, and/or V-V pacing escape intervals, an AV delay interval timer 372 for timing an AV delays from a preceding A-EVENT (SAV) or A-TRIG (PAV), a post-event timer 374 for timing post-ventricular time periods, and a date/time clock 376. RHC pace trigger and sense events are typically used for starting and resetting these intervals and periods. However, it would be possible to allow the physician to select and program trans-chamber or LHC pace trigger and sense events for these timing purposes.

The post-event timer 374 times out the post-ventricular time periods following an RV-EVENT, LV-EVENT, RV-TRIG, or LV-TRIG event. Similar post-atrial time periods are timed following an A-EVENT or A-TRIG. The durations of the post-event time periods may also be selected as programmable parameters stored in the microcomputer 302. The post-ventricular time periods include the PVARP, a post-atrial ventricular blanking period (PAVBP), a ventricular blanking period (VBP), and a ventricular refractory period (VRP). The post-atrial time periods include an atrial refractory period (ARP) during which an A-EVENT is ignored for the purpose of resetting the AV delay, and an atrial blanking period (ABP) during which atrial sensing is disabled. These post-atrial time periods time out concurrently with the time-out of the SAV or PAV delay started by an A-EVENT or an A-TRIG.

It should be noted that the starting of the post-atrial time periods and the AV delays can be commenced substantially simultaneously with the start or end of the A-EVENT or the A-TRIG or, in the latter case, upon the start of end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the start of end of the V-PACE which may follow the V-TRIG.

The microprocessor 304 also optionally calculates AV delays, post-ventricular time periods, and post-atrial time periods that vary with the sensor based escape interval established in response to the RCP(s) and/or with the intrinsic atrial rate. The variable AV delays are usually derived as a fraction of a maximum AV delay set for the pacing LRL (i.e., the longest escape interval).

The output amplifiers circuit 340 contains a RA pace pulse generator (and a LA pace pulse generator if LA pacing is provided), a RV pace pulse generator, and a LV pace pulse generator corresponding to any of those presently employed in commercially marketed cardiac pacemakers providing atrial and ventricular pacing. In order to trigger generation of an RV-PACE or LV-PACE pulse, digital controller/timer circuit 330 generates a RV-TRIG or LV-TRIG signal at the end of a paced AV (PAV) delay or a sensed AV (SAV) delay provided by AV delay interval timer 372. Similarly, digital controller/timer circuit 330 generates an RA-TRIG signal that triggers output of an RA-PACE pulse (or an LA-TRIG signal that triggers output of an LA-PACE pulse if provided) at the end of the V-A escape interval timed by escape interval timers 370.

The output amplifiers circuit 340 includes switching circuits for coupling selected pace electrode pairs from among the lead conductors and the IND_CAN electrode 20 to the RA pace pulse generator (and LA pace pulse generator if provided), RV pace pulse generator and LV pace pulse generator. Pace/sense electrode pair selection and control circuit 350 selects lead conductors and associated pace electrode pairs to be coupled with the atrial and ventricular output amplifiers within output amplifiers circuit 340 for accomplishing RA, LA, RV and LV pacing.

The sense amplifiers circuit 360 contains sense amplifiers corresponding to any of those presently employed in commercially marketed cardiac pacemakers for atrial and ventricular pacing and sensing. As noted in the above-referenced, commonly assigned, '324 patent, it has been common in the prior art to use very high impedance P-wave and R-wave sense amplifiers to amplify the voltage difference signal which is generated across the sense electrode pairs by the passage of a cardiac depolarization. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 330 controls sensitivity settings of the atrial and ventricular sense amplifiers 360.

The sense amplifiers are uncoupled from the sense electrodes during the blanking periods before, during, and after delivery of a pace pulse to any of the pace electrodes of the pacing system to avoid saturation of the sense amplifiers. The sense amplifiers circuit 360 includes blanking circuits for uncoupling the selected pairs of the lead conductors and the IND_CAN electrode 20 from the inputs of the RA sense amplifier (and LA sense amplifier if provided), RV sense amplifier and LV sense amplifier during the ABP, PVABP and VBP. The sense amplifiers circuit 360 also includes switching circuits for coupling selected sense electrode lead conductors and the IND_CAN electrode 20 to the RA sense amplifier (and LA sense amplifier if provided), RV sense amplifier and LV sense amplifier. Again, sense electrode selection and control circuit 350 selects conductors and associated sense electrode pairs to be coupled with the atrial and ventricular sense amplifiers within the output amplifiers circuit 340 and sense amplifiers circuit 360 for accomplishing RA, LA, RV and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 330. Similarly, left atrial depolarizations or P-waves in the LA-SENSE signal that are sensed by the LA sense amplifier, if provided, result in an LA-EVENT signal that is communicated to the digital controller/timer circuit 330. Ventricular depolarizations or R-waves in the RV-SENSE signal are sensed by a ventricular sense amplifier and result in an RV-EVENT signal that is communicated to the digital controller/timer circuit 330. Similarly, ventricular depolarizations or R-waves in the LV-SENSE signal are sensed by a ventricular sense amplifier and result in an LV-EVENT signal that is communicated to the digital controller/timer circuit 330. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

To simplify the description of FIGS. 4 through 6A–6B, it will be assumed that the following references to an "A-EVENT" and "A-PACE" will be the RA-EVENT and RA-PACE, respectively, if there is no LA pacing or sensing provided, or if the LA pacing or sensing is not programmably enabled. If LA pacing or sensing is provided or programmably enabled, the "A-EVENT" and "A-PACE" will refer to the programmed one of the RA-EVENT or LA-EVENT and RA-PACE or LA-PACE, respectively.

In accordance with one embodiment of the present invention, the V-V conduction time between first and second ventricular sites, e.g., the sites where the RV and LV pace/sense electrodes are lodged, is periodically timed out by the intrinsic interval timers 368. The measured RV-LV and/or LV-RV conduction time is stored in RAM 310 developing trend data for subsequent uplink telemetry and analysis by a treating physician. The pacing system is operated in an RV triggered pacing mode wherein an RV-PACE or LV-PACE is delivered either at the time-out of the SAV or PAV delay or upon a non-refractory RV event during the time-out of the SAV or PAV delay.

The possible operating modes of IPG circuit 300 are depicted in the flow chart of FIG. 4 and described as follows. The particular operating mode of the present invention is a programmed or hard-wired sub-set of the possible operating modes as also described below. The AV delay is started in step S100 when a P-wave outside of refractory is sensed across the selected atrial sense electrode pair during the V-A escape interval (an A-EVENT) as determined in step S134 or an A-PACE pulse is delivered to the selected atrial pace electrode pair in step S118. The AV delay can be a PAV or SAV delay, depending upon whether it is started on an A-PACE or an A-EVENT, respectively, and is timed out by the SAV/PAV delay timer 372. The SAV or PAV delay is terminated upon a non-refractory RV-EVENT or LV-EVENT output by a ventricular sense amplifier prior to its time-out.

In step S104, the post-event timers 374 are started to time out the post-ventricular time periods and the TRIG_PACE window, and the V-A escape interval timer 370 is started to time out the V-A escape interval if the SAV or PAV delay times out in step S102 without the detection of a non-refractory RV-EVENT or LV-EVENT. The TRIG_PACE window inhibits triggered pacing modes in response to a sense event occurring too early in the escape interval.

Either a programmed one or both of the RV-PACE and LV-PACE pulses are delivered in step S106 (as shown in the flow chart of FIG. 5) to selected RV and LV pace electrode pairs, and the V-A escape interval timer is timed out in step S116. When both of the RV-PACE and LV-PACE pulses are delivered, the first is referred to as V-PACE1, the second is referred to as V-PACE2, and they are separated by a VP-VP delay. As described in greater detail below in reference to FIGS. 6A–6B, if a bi-ventricular pacing mode is programmed in step S106, it can be selectively programmed in a left-to-right or right-to-left ventricle pacing sequence wherein the first and second delivered ventricular pace pulses are separated by separately programmed VP-VP delays. The VP-VP delays are preferably programmable between about 4 msec and about 80 msec.

Figure 6A:
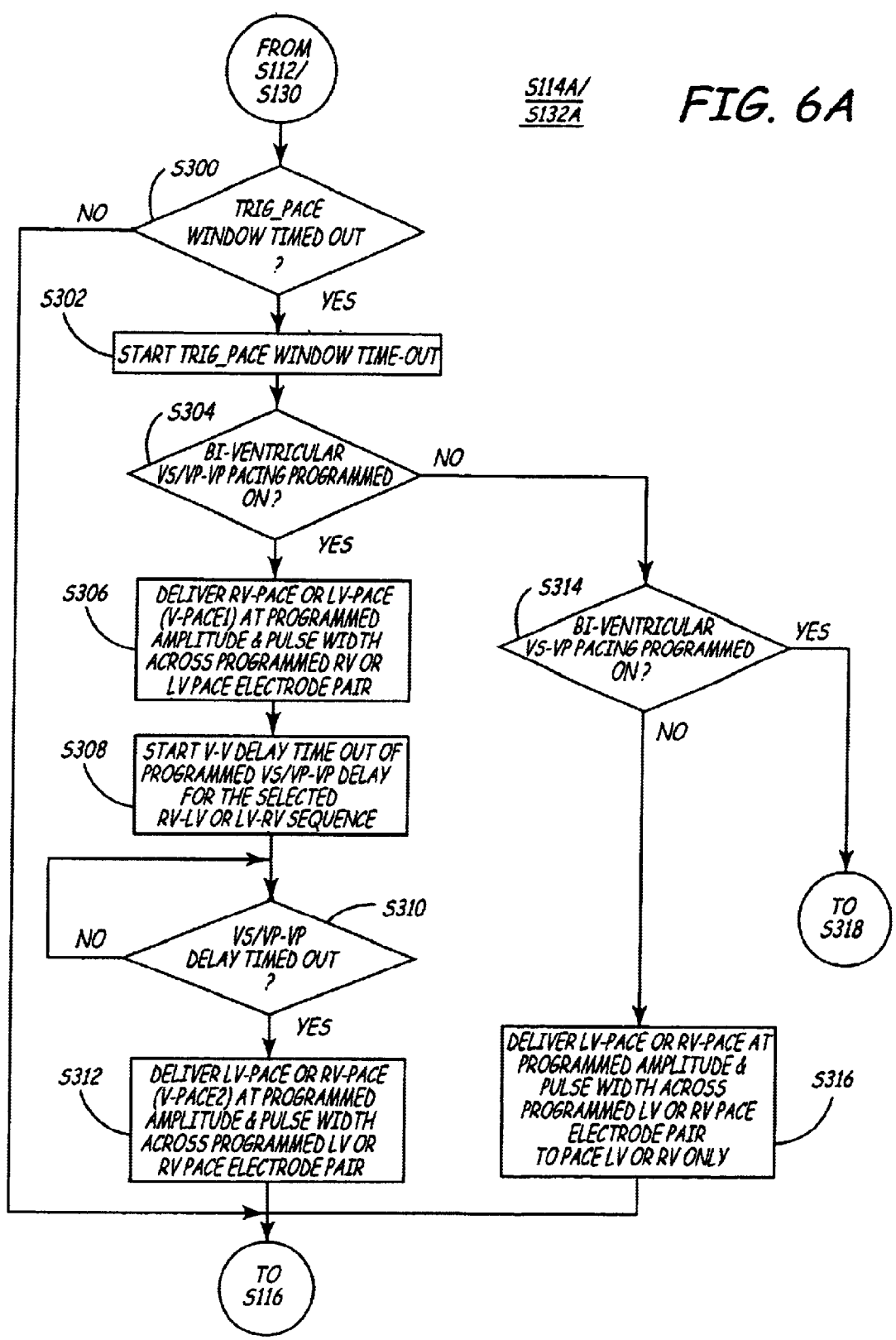
FIGS. 6A–6B is a flow chart illustrating the steps of delivering ventricular pace pulses following a ventricular sense event during the time-out of an AV delay or the V-A escape interval in FIG. 4.
Figure 6B:
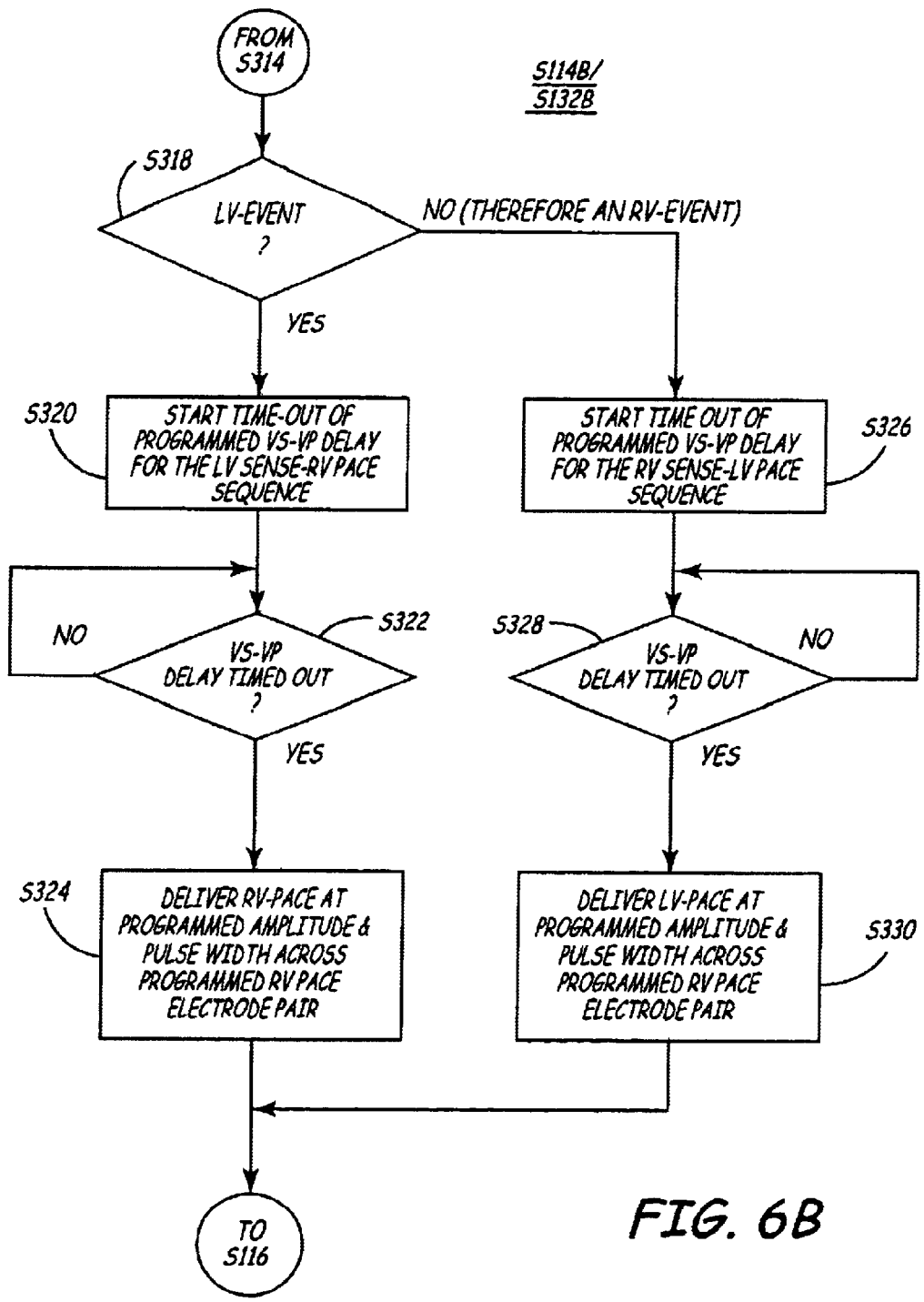

Returning to step S102, the AV delay is terminated if an RV-EVENT or LV-EVENT (collectively, a V-EVENT) is generated by the RV sense amplifier or the LV sense amplifier in step S108. The time-out of the V-A escape interval and the post-ventricular time periods are started in step S110 in response to the V-EVENT. In step S112, it is determined whether a ventricular triggered pacing mode is programmed to be operative during the AV delay. If a ventricular triggered pacing mode is programmed on, it is undertaken and completed in step S114 (FIGS. 6A–6B). Any VSP mode that may otherwise be available is programmed off. The time-out of the TRIG_PACE window is commenced in step S113 simultaneously with the time-out of the V-A escape interval and post-event time periods in step S110.

In accordance with an aspect of the present invention, the ventricular triggered pacing mode can be turned ON or OFF so that step S112 is set to YES or NO, respectively, during the V-V conduction time measurement.

If the V-A atrial escape interval is timed out by timer 370 in step S116 without a non-refractory A-EVENT being sensed across the selected pair of atrial sense electrodes, then the A-PACE pulse is delivered across the selected RA pace electrode pair in step S118, the AV delay is set to PAV in step S120, and the AV delay is commenced by AV delay timer 372.

If a non-refractory A-EVENT is sensed as determined in steps S122 and S134, then the V-A escape interval is terminated. The ABP and ARP are commenced by post-event timers 374 in step S134, the AV delay is set to the SAV in step S138, and the SAV delay is started in step S100 and timed out by SAV/PAV delay timer 372.

Assuming that the goal is to restore the normal activation sequence, a programmed SAV and PAV delay corresponding to a normal AV conduction time from the AV node to the bundle of His may be used. Alternatively, SAV/PAV delay timer 372 may calculate SAV and PAV delays based on a prevailing sensor rate or sensed intrinsic heart rate.

In step S123, it is determined whether an RV-EVENT or LV-EVENT (hereinafter, referred to as "V-EVENT" for simplicity) is sensed across the RV or LV pace/sense electrodes during the time-out of the V-A escape interval. In step S124, it is determined if the V-EVENT is a non-refractory V-EVENT or a refractory V-EVENT. If the V-EVENT is determined to be a non-refractory V-EVENT in step S124, the TRIG_PACE window is started or restarted, the V-A escape interval is restarted, and the post-ventricular time periods are restarted in step S126.

Whether a ventricular triggered pacing mode is programmed to be operative during the V-A escape interval is determined in step S128. Ventricular triggered pacing during the V-A escape interval is not enabled, or may not be provided in the pacing system at all, when triggered ventricular pacing is inappropriate for the patient. If ventricular triggered pacing during the V-A escape interval is programmed on, then it is undertaken and completed in step S132 (FIGS. 6A–6B). If triggered pacing is not programmed on as determined in step S130, then no ventricular pacing is triggered by the sensed non-refractory V-EVENT during the V-A escape interval.

In accordance with an aspect of the present invention, the ventricular triggered pacing mode can be turned ON or OFF so that step S128 is set to YES or NO, respectively, thereby suspending time-out of the V-V delay timer and delivery of a V-PACE 2 upon its time-out when the V-V conduction time is to be measured. This enables the V-V conduction time measurement to either commence from an intrinsic V-EVENT or a V-PACE. Preferably, the V-EVENT is the RV-EVENT, the V-PACE is the RV-PACE, and the V-V conduction time is the RV-LV conduction time from an RV-EVENT or an RV-PACE to an LV-EVENT sensed following the expiration of the blanking and refractor periods.

Figure 5:
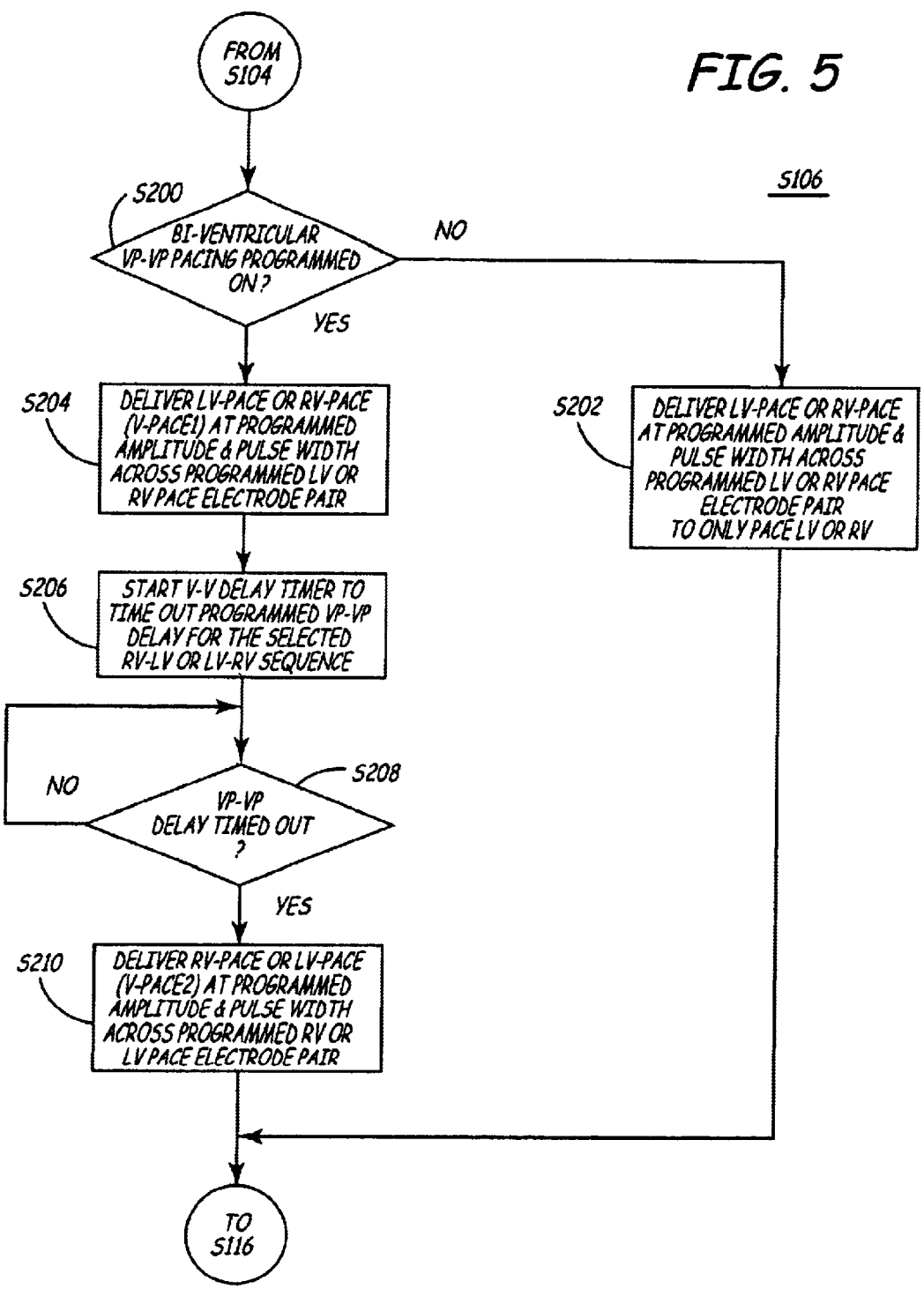
FIG. 5 is a flow chart illustrating the steps of delivering ventricular pace pulses following time-out of an AV delay in FIG. 4.

FIG. 5 depicts the step S106 in greater detail, and FIGS. 6A-6B depict the steps S114 and S132 in greater detail. If a VP-VP pacing mode is programmed on in step S106, it can be selectively programmed in a left-to-right or right-to-left ventricle sequence, wherein the first and second delivered ventricular pace pulses (V-PACE1 and V-PACE2) are separated by separately programmed VP-VP delays. If a bi-ventricular triggered pacing mode is programmed on in either or both of steps S114 and S132, it can be selectively programmed to immediately pace the ventricle from which the V-EVENT is sensed or a fixed or programmed ventricle regardless of where the V-EVENT is sensed with a V-PACE1. Then, the V-PACE2 is generated to synchronously pace the other ventricle after a programmed VS/VP-VP delay. Or, the triggered pacing mode can be selectively programmed in either or both of steps S114 and 132 to only synchronously pace the other ventricle than the ventricle from which the V-EVENT is sensed with V-PACE2 after separately programmable VS-VP delays, depending on the right-to-left or left-to-right sequence. All of these VP-VP, VS/VP-VP, and VS-VP delays are preferably programmable between nearly 0 msec and about 80 msec.

As a practical matter, the minimum VS/VP-VP, and VP-VP delays may be set to one half the system clock cycle in order to avoid simultaneous delivery of RV-PACE and LV-PACE pulses. The pace pulse width is typically programmable between about 0.5 msec and 2.0 msec, and the pace pulse amplitude is typically programmable between 0.5 and 7.5 volts. The system clock provides a full clock cycle of about 8.0 msec. Therefore, the minimum VP-VP delay is set at a half clock cycle or about 4.0 msec.

As shown in FIG. 5, the IPG circuit 300 of FIG. 3 can be programmed to either only deliver a single RV-PACE or LV-PACE (V-PACE1) or the pair of RV-PACE and LV-PACE pulses (V-PACE1 and V-PACE2) separated by the VP-VP delay timed out by V-V delay timer 366. If delivery of only a single RV-PACE or LV-PACE is programmed as determined in step S200, then it is delivered in step S202.

If VP-VP pacing is programmed on and not set to NO in step S200, then V-PACE1 is delivered in step S204 in the programmed RV-LV or LV-RV sequence. Again, the RV-PACE pulse is typically delivered across the active RV tip electrode 40 and one of the available indifferent electrodes that is programmed and selected through the pace/sense electrode selection and control 350 depending on the desired RV pacing vector as set forth above, and also on which electrodes are present in the system. The LV-PACE pulse is delivered across the active LV pace electrode 50 and the IND_RV pace electrode 38 in the trans-ventricular pacing path 60. The V-PACE1 pace pulse is delivered at a programmed pulse energy dictated by the programmed voltage and pulse width.

The V-V delay timer 366 is loaded with the programmed VP-VP delay and starts to time out in step S206. If the RV-PACE pulse is V-PACE1, then a programmed VP-VP delay is timed in V-V delay timer 366. The LV-PACE pulse is delivered as V-PACE2 in the LV pacing path 60 between the active LV pace electrode 50 and IND_RV pace electrode 38 in step S210 after time-out of the programmed VP-VP delay in step S208. Conversely, if the LV-PACE pulse is the first to be delivered (V-PACE1) in the pacing path 60, then a programmed VP-VP delay is timed in V-V delay timer 366. The RV-PACE pulse is then delivered as V-PACE2 typically across the active RV pace electrode 40 and the programmed indifferent electrode in step S210 after time-out of the programmed VP-VP delay in step S208.

In accordance with one embodiment of the present invention, step S206 is not timed out or steps S206–S210 are bypassed so that no V-PACE2 is delivered and the intrinsic or paced conduction time can be measured. The time out of the VP-VP delay and delivery of the V-PACE2 are thereby suspended.

Figure 4:
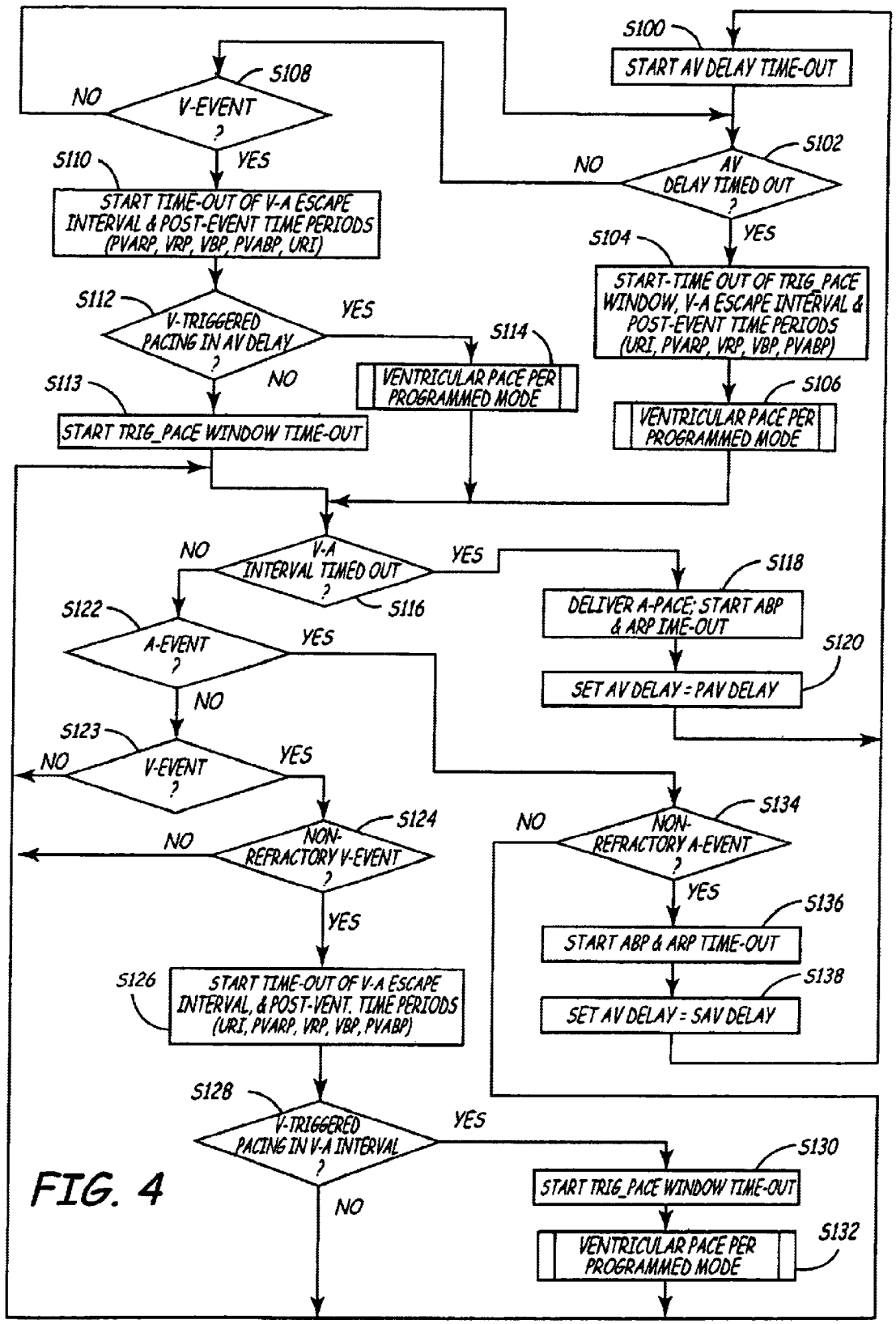
FIG. 4 is a comprehensive flow-chart illustrating the operating modes of the IPG circuitry of FIG. 3 in a variety of AV synchronous, bi-ventricular pacing modes in accordance with one embodiment of the invention.

FIGS. 6A–6B is a flow chart illustrating the steps S114 and S132 of FIG. 4 (when provided or enabled) for delivering ventricular pace pulses triggered by a ventricular sense event in step S108 during the time-out of an AV delay or in step S124 during time-out of the V-A escape interval. As noted above, the sensing of R-waves in the RV and LV can be accomplished by employing several RV-SENSE and LV-SENSE sensing axes or vectors and the trans-ventricular sensing vector. These vectors may include a bipolar RV-SENSE vector (RV sense electrodes 38 and 40), a unipolar RV-SENSE vector (RV tip sense electrode 40 and IND_CAN electrode 20), a unipolar LV-SENSE vector (LV sense electrode 50 and IND_CAN electrode 20), and a trans-ventricular, combined RV-SENSE and LV-SENSE vector (RV tip sense electrode 40 and LV sense electrode 50) can be programmed. The selection of the sensing vectors would depend upon heart condition and the selection of the pace pulse pathways.

The IPG circuit 300 can be separately programmed in one of three triggered pacing modes designated VS/VP, VS/VP-VP or VS-VP triggered modes for step S114. In the VS/VP triggered pacing mode, a V-PACE1 is delivered without delay upon a RV-EVENT or LV-EVENT to the RV or LV pacing pathway, respectively. In the VS/VP-VP triggered pacing mode, the V-PACE1 is delivered without delay upon a RV-EVENT or LV-EVENT to the selected RV or LV pacing electrode pair, respectively, and a V-PACE2 is delivered to the other of the selected LV or RV pacing electrode pair after the VS/VP-VP delay times out. In the VS-VP pacing mode, a RV-EVENT or the LV-EVENT starts time-out of a VS-VP delay, and a single pace pulse (designated V-PACE2) is delivered to the selected LV or the RV pace electrode pair, respectively, when the VS-VP delay times out.

The TRIG_PACE time window started by a prior V-EVENT or V-PACE must have timed out in step S300 prior to delivery of any triggered ventricular pace pulses. If it has not timed out, then triggered pacing cannot be delivered in response to a sensed V-EVENT. If the TRIG_PACE window has timed out, it is then restarted in step S302, and the programmed triggered pacing modes are checked in steps S304 and S316.

When IPG circuit 300 is programmed in the VS/VP-VP triggered mode as determined in step S304, the non-refractory RV-EVENT or LV-EVENT or collective V-EVENT of indeterminable origin is treated as a single V-EVENT. If the TRIG_PACE window has timed out as determined in step S300, then the single V-EVENT triggers the immediate delivery of a programmed one of the RV-PACE or a LV-PACE as V-PACE1 across the programmed bipolar or unipolar RV and LV pace electrode pair, respectively, in step S306. Thus, V-PACE1 is delivered to a predetermined RV or LV pace electrode pair, regardless of whether a RV-EVENT and LV-EVENT is sensed.

Then, a VS/VP-VP delay is started in step S308 and timed out in step S310. The VS/VP-VP delay is specified as a VP-VP delay when the RV-PACE is V-PACE1 and the LV-PACE is V-PACE2. The VS/VP-VP delay is specified as a VP-VP delay when the LV-PACE is V-PACE1 and the RV-PACE is V-PACE2. The LV-PACE or RV-PACE pulse is delivered at the programmed amplitude and pulse width across the programmed LV or RV pace electrode pair in step S210.

In accordance with one embodiment of the present invention, step S308 is not timed out or steps S308–S312 are bypassed so that no V-PACE2 is delivered and the intrinsic conduction time can be measured. The time out of the VS/VP-VP delay and delivery of the V-PACE2 are thereby suspended.

In step S314, it is determined whether the VS-VP triggered pacing mode or the VS/VP triggered pacing mode is programmed ON. When the IPG circuit 300 is programmed to a single heart chamber VS/VP triggered pacing mode, the RV-EVENT or LV-EVENT triggers the immediate delivery of an RV-PACE or an LV-PACE across a programmed bipolar or unipolar RV or LV pace electrode pair, respectively, in step S316, regardless of whether an RV-EVENT or LV-EVENT was sensed.

When the IPG circuit 300 is programmed to the VS-VP triggered pacing mode, an LV-EVENT as determined in step S318 loads the appropriate VS-VP delay in V-V delay timer 366 in step S320 and starts the VS-VP delay time-out in step S322. The RV-PACE is delivered at its time-out in step S322 (also designated V-PACE2). If an RV-EVENT is determined in step S318, then the appropriate VS-VP delay in V-V delay timer 366 is determined in step S326, and the VS-VP delay is timed out in step S328. The LV-PACE (also designated V-PACE2) is delivered at time-out of the VS-VP delay in step S330.

In all of steps S306, S312, S316, S324 and S330, the LV-PACE pulse is preferably delivered as V-PACE2 in the LV pacing path 60 between the active LV pace electrode 50 and IND_RV pace electrode 38.

In accordance with one embodiment of the present invention, step S314 is set to "NO" or the steps S320 and S326 are not timed out during the measurement of the V-V conduction time so that no V-PACE2 is delivered and the intrinsic conduction time can be measured. The time-out of the VS-VP delay and delivery of the V-PACE2 are thereby suspended.

Returning to FIG. 4, the V-A escape interval is timed out in step S116 following the completion of the ventricular pacing mode of FIGS. 6A–6B. If the V-A escape interval times out, then an RA-PACE pulse is typically first delivered across the RA pace electrodes 17 and 19 in step S118, and the AV delay timer is restarted in step S100. The duration of the V-A or V-V escape interval is continually varied between the URI and the LRI and the PAV and SAV are varied between AV delay limits as a function of the activity sensor output signal PAS indicating the need for cardiac output based upon patient activity level.

V-V Conduction Time Measurement and Storage.

Thus, it will be observed that the multi-site, AV sequential, bi-ventricular cardiac pacing system described above is selectively programmable to provide ventricular pacing pulses delivered to one or both of the RV and LV sites synchronously within a V-V pace delay following time-out of an AV delay from a preceding delivered A-PACE pulse or an A-EVENT (typically, the RA-PACE pulse or the RA-EVENT) and operating in accordance with the steps of: (a) timing an AV delay from a preceding delivered A-PACE pulse or A-EVENT; (b) detecting a V-SENSE at one of a first and second ventricular site within the AV delay and, in response, terminating the AV delay and providing a V-EVENT; (c) delivering a V-PACE1 pulse to a selected one of the first and second ventricular sites upon the time-out of the AV delay or, in a triggered mode, upon the V-SENSE; (d) timing a V-V pace delay comprising one of a VS-VP pace delay from a V-EVENT occurring prior to the time-out of the AV delay or a VP-VP pace delay from the V-PACE1 delivered at the end of the AV delay or a VS/VP-VP pace delay from a triggered V-PACE1; and (e) delivering a V-PACE2 pulse to the other of the first and second ventricular sites upon the time-out of the V-V pace delay.

Figure 8:
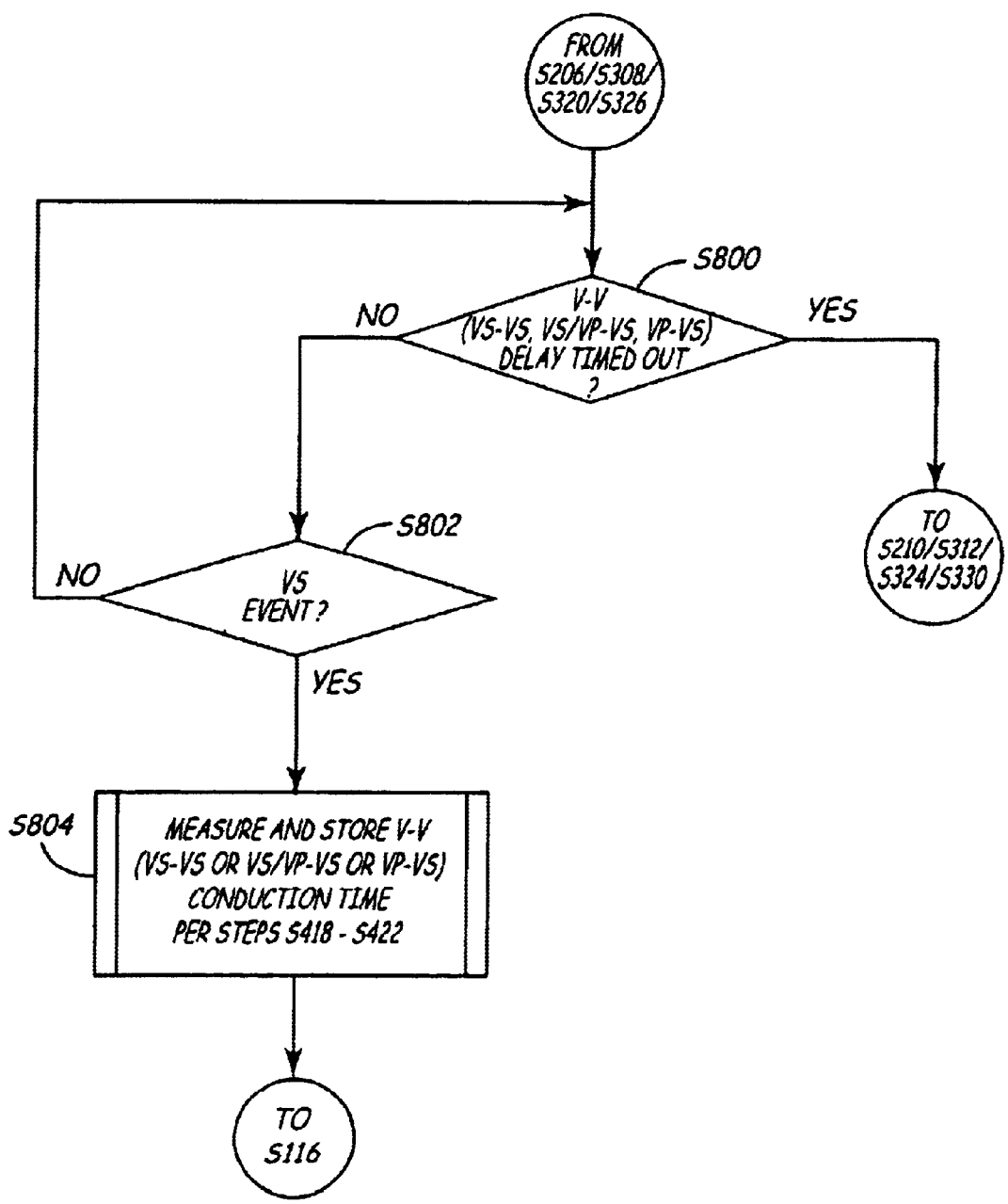
FIG. 8 is a flow chart illustrating an alternative manner of instituting the measurement and storage of the V-V conduction time data.

These normal operating modes are interrupted to perform the V-V conduction time measurements in a manner depicted in FIGS. 7 and 8. In one variation of the invention, the V-V conduction time measurement mode causes the triggered pacing mode to be entered wherein step (b) is modified by delivering a ventricular pace pulse to the selected one of the RV and LV site upon the detection of the ventricular depolarization during the time-out of the AV delay or upon expiration of the AV delay, steps (d) and (e) are suspended (in this case are not started or bypassed as noted above), and a measurement of the intrinsic VS/VP-VS conduction time elapsing from the delivery of the ventricular pace pulse to the selected one of the RV and LV sites and the detection of the conducted depolarization at the other of the RV and LV site is made and stored in memory.

In a further variation, the triggered pacing mode is not entered, and the intrinsic ventricular rate examined to ensure that it is above the programmed LRL such that the ventricular depolarization consistently falls within the prevailing AV delay and inhibits delivery of a ventricular pacing pulse at the timeout of the AV delay. Steps (d) and (e) are suspended, the VS-VS conduction time between the sensed ventricular depolarization at the selected one of the RV and LV site and the subsequent ventricular depolarization at the other one of the RV and LV site is measured, and the elapsed VS-VS conduction time is stored in memory.

In a still further variation, an overdrive pacing mode is entered that synchronously paces the atrial chamber and the selected one of the RV and LV sites at a rate exceeding the prevailing intrinsic heart rate to ensure capture. Steps (d) and (e) are suspended, and a measurement of the VP-VS conduction time elapsing from the delivery of the ventricular pace pulse to the selected one of the RV and LV sites and the detection of the conducted depolarization in the other of the RV and LV sites is made and stored in memory.

FIG. 7 illustrates the overall IMD function starting from the time of implantation (step S400), initial programming (steps 402) and baseline parameter measurements (step S404). Processing is shown to continue through successive cycles of gathering parameter data in the IMD (steps S406–S426), and uplink telemetry transmission of the accumulated data to an external programmer (steps S428–S430) for display and analysis (step S432). This may result in the possible reprogramming (step S402) and baseline parameter measurement (step S404) to better assess the heart failure state. The present invention may be implemented into a versatile multi-chamber pacing system as described above or into a less comprehensive pacing system offering fewer programmable pacing parameters and operating modes.

Each measured parameter may be programmably enabled, with a particular selected event trigger initiating measurement of the enabled parameters. Specific measurement criteria may be programmed in step S402 using conventional downlink telemetry transmitted commands that are received in the telemetry transceiver 332 and forwarded to the digital controller/timer circuit 330. The physician may initially program the pacemaker to deliver a bi-ventricular stimulation therapy in accordance with options provided in the flow charts of FIGS. 4, 5 and 6A–6B as described above wherein triggered VS/VP ventricular pacing may be programmed ON or OFF. However, the programmed mode may be temporarily switched to gather V-V data related to all possible modes in step S426.

In step S404, baseline parameter measurements are optionally performed for each programmably-enabled parameter to collect baseline or reference parameter data, particularly the selected ones of the V-V conduction times (including the VP-VS, VP/VS-VS and/or VS-VS conduction times). This data may be stored in RAM 310 and transferred to an external programmer for observation by the physician and to use it to program the operating modes and parameter values. The initial and updated baseline parameter measurements can be stored in IMD RAM registers and/or stored externally in a patient file maintained by the physician with a date and time stamp and other pertinent data such as patient activity level measured by activity signal processor circuit 332 and patient heart rate.

After implant, the enabled parameters are measured when an event trigger for the specific parameter occurs, the pacing system is operating in its programmed pacing mode, and when heart rate and/or rhythm criteria are met as set forth in steps S406–S412. The event of step S406 may include one or more predetermined times of every day, or alternatively, may include specified days of the week or month as tracked by the date/time clock 376. In another embodiment, the event criteria may involve detection of a patient-initiated parameter measurement or some other programmed event. According to yet another embodiment, a combination of the time or times of day and a level of patient exercise indicated by the activity signal processor circuit 332 may be utilized as the trigger. The event criteria of step S406 cannot be satisfied if the pacing mode is not in the programmed pacing mode, which can occur if a telemetry session is underway, or a mode switch has taken place due to application of a magnetic field to a magnetic field sensor in a manner well known in the art.

Typically, the measurement of the V-V conduction time should take place when the heart rate is in a normal range and is stable within a certain stability tolerance which can both be programmed by the physician and are determined over a series of heart cycles in steps S408–S412 in a manner well known in the art. The measurement of the V-V conduction time also only takes place in step S416 when the patient is at rest or exhibits no more than a certain programmable level of activity as determined in step S414. Typically, in step S408, incidences of spontaneous RA-EVENTs and RV-EVENTs would be monitored while the escape interval establishing the pacing rate is set to the LRI to determine the intrinsic heart rate.

The heart rate would be established at the pacing LRL or another programmed rate in step S412 if the intrinsic heart rate cannot be determined in this way or is unstable as determined in step S410. The atrial and ventricular pacing pulses will be delivered during the test if the patient's intrinsic heart rate is lower than the LRI established pacing rate, and consequently the heart rate will be inherently low and stable under these circumstances. However, in this case, only the VP-VS conduction time can be determined in the particular measurement session commenced in step S406.

The prevailing V-V delay time-out is suspended in step S416 in any of the ways described above when the programmed activity level criteria are met in step S414 and the preceding criteria are satisfied. Measurement and storage of the particular one of the VS-VS or VS/VP-VS and VP-VS conduction times is then conducted in steps S418–S422. The heart rate and/or stability continues to be monitored through steps S418–S426. The VS-VS or VS/VP-VS conduction time measurement that is commenced in step S416 may also be aborted if the heart rate and/or stability changes such that the heart rate/stability criteria become no longer satisfied in step S410 before the parameter measurement steps are completed. Heart rate instability or sudden elevation would not normally constitute a problem in the present case, because the VS-VS or VS/VP-VS conduction time can be accomplished in a single heart cycle. But, such measurements might be halted if the heart rate suddenly becomes high or unstable during the process of deriving an average VS-VS or VS/VP-VS conduction time value over several heart cycles.

Despite setting forth these criteria, it will be understood that any one or more or none of these criteria of steps S406–S414 or other criteria found useful in the clinical setting can be employed in the practice of the invention.

The physician may program the IMD to perform one or more of the VS-VS, VP-VS and VS/VP-VS conduction time measurements in a single session initiated in step S406. In each case, a single conduction time value can be measured in step S418 and directly stored in RAM registers in step S422. The measurement can be effected in a clocked hardware timer or a software algorithm or may simply be represented by stored start and stop cycle counts or any other manner known in the art. Additionally or alternatively, the maximum, minimum and average conduction time values can be obtained in steps S418–S420 by repeating the measurement step S418 over a programmable number of consecutive heart cycles to obtain and temporarily store a plurality of the VS-VS, VP-VS and VS/VP-VS conduction time measurements. The processing of the maximum, minimum and average conduction time values from the temporarily stored, successively measured, conduction time values takes place in step S420, and the resulting values are stored in RAM registers in step S422.

A determination of whether all such programmed measurement modes are completed is made in step S424. The pacing mode is switched in step S426 to the next mode to repeat steps S414–S424 (or steps S408–S424) if all programmed modes are not yet completed. The completed V-V conduction time data is stored in IMD memory with a date and time stamp and any other pertinent information, e.g., patient activity level, intrinsic heart rate, etc., in step S418. The history of the number, times and dates of successive parameter measurements can also be stored in IMD memory, but the stored parameter data and related data may be discarded on a FIFO basis if the memory capacity assigned to such data storage is exceeded.

Steps S406 through S426 are repeated each time that the event trigger criteria for the V-V conduction time measurement are satisfied. The data collection continues until the accumulated data is uplink telemetered to the physician in steps S428 and S430. The physician then reviews the accumulated data in step S432 to determine if the V-V conduction times reveal a trend. RV-LV trend data evidencing any change in the intrinsic or triggered V-V conduction time between RV and LV sites gathered over a period of days, weeks and months provides a valuable indication as to whether the heart failure state is improving, worsening or staying about the same. The physician can then reprogram pacing operating modes and parameter values in steps S402 and S404 to provide a more efficacious therapy.

As noted above, certain of the steps of the flow charts of FIGS. 4 through 6A–6B can be suspended when V-V conduction times are measured from a first V-EVENT, a V-PACE1 or VS/VP in the first ventricular heart chamber, and this mode of operation is described above in reference to FIG. 7. The normal VS-VP, VS/VP-VP and VP-VP operating modes depicted in FIGS. 4 through 6A–6B (that is, the modes wherein measuring the V-V conduction time is not operative) assume that the inherent V-V conduction time is about equal to or longer than the programmed V-V delay.

In the above-referenced '324 patent, a non-refractory ventricular sense event detected at either the right or left ventricular pace/sense electrodes starts the prevailing V-V delay or CDW timer during the AV delay and during a V-A escape interval as described above in the steps of the flow charts of FIGS. 4 through 6A–6B. The V-PACE2 pulse is delivered to the other of the left or right ventricular pace/sense electrodes at the time-out of the prevailing V-V delay or CDW, but is inhibited if a V-SENSE event is detected at that site while the CDW times out.

Thus, in a further embodiment of the present invention, the measurement of one or more of the VS-VS, VS/VP-VS and VP-VS conduction times can involve measuring the elapsed time from a VS or VP at the first ventricular site until the detection, during time-out of the V-V delay, of the VS event at the second ventricular site that terminates the V-V delay without delivery of the second VP pulse. Thus, FIG. 8 depicts an alteration of the indicated steps of FIGS. 4 through 6B wherein step S800 represents steps S208 timing out the VP-VP delay, step S310 timing out the VS/VP-VP delay, and steps S322 and S328 each timing out the VS-VP delay of FIGS. 5 and 6A–6B. In this case, a VS event that is sensed at the second ventricular site (e.g., either the RV or LV site) in step S802 prior to the time-out of the applicable one of the VS-VP, VS/VP-VP or the VP-VP delay terminates that time-out. The applicable VS-VS, VS/VP-VS or the VP-VS conduction time is measured in step S804 in the manner described above in respect to steps S406–S426 of FIG. 7. These times can be followed to develop trend data.

In this regard, the criteria establishing steps S406–S414 can be selectively programmed to establish any one or all or none or equivalent other criteria precedent to, or triggering measurement and storage of, the V-V conduction data. Steps S424 and S426 can be programmed to effect selective temporary mode setting to obtain the data when the triggering criteria are satisfied.

The preceding specific embodiments are directed to RV and LV pacing in a predetermined sequence at ventricular sites in the RV and LV. However, it will be understood that the present invention also embraces locating first and second ventricular pace/sense electrodes separated apart from one another but within either the RV or LV.

RHC-LHC/LHC-RHC Conduction Time Measurement and Storage.

Figure 9:
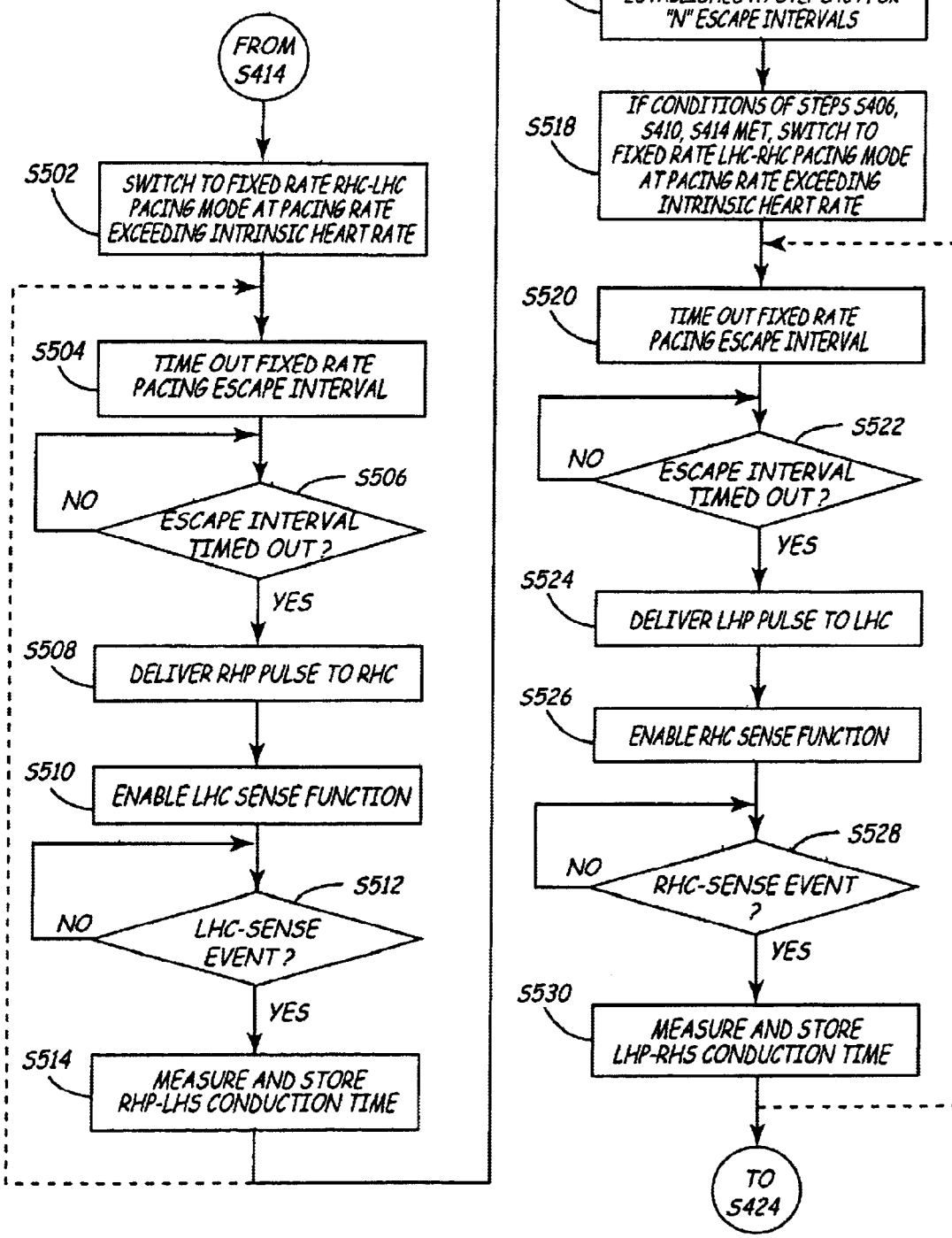
FIG. 9 is a flow chart illustrating alternative steps for periodically determining RHC-LHC and LHC-RHC conduction times in steps S416 and S422 of FIG. 7.

The above-described three or four chamber pacing system of FIGS. 2–8 can be employed as stated at the outset to derive, process and store A-A conduction times between the RA and LA pace/sense electrodes instead of, or in addition to, the above-described V-V conduction times. FIG. 9 sets forth steps that can be undertaken in substitution for steps S416 and S422 of FIG. 7 to measure and store one or both of RHC-LHC and LHC-RHC conduction times wherein RHC can be the RV or RA and LHC can be the LV or LA, respectively.

The RHC-LHC and LHC-RHC conduction time measurements can be made from intrinsic sense events at the first RHC or LHC site to an intrinsic sense event at the second LHC and RHC, respectively, site. Preferably, the first site is paced at the time-out of a pacing escape interval or upon a sense event. In this way an RHP-LHC conduction time is measured from an RHC pace (RHP) pulse to an LHC sense (LHS) event and an LHP-RHC conduction time is measured from an LHC pace (LHP) pulse to an RHC sense (RHS) event. The RHP-LHC conduction time can be compared with the LHP-RHC conduction time in the assessment of the heart failure state.

Thus, in FIG. 8, when the criteria of steps S406–S414 are met, the pacing mode is switched to a fixed rate pacing mode that overdrives the intrinsic heart rate in the upper or lower heart chambers in step S502. Thus, either an A-A or V-V pacing escape interval is established in step S502, and the escape interval is timed out in step S504. An RHP pulse is delivered in step S508 to the RHC when the escape interval times out as determined in step S506. The LHC sense amplifier is enabled in step S510, typically after a blanking period, to detect the conducted depolarization that arrives at the LHC pace/sense electrodes in step S512. The RHP-LHS conduction time is measured and stored in step S514. Steps S504–S514 can be repeated via the broken line path so that a series of RHP-LHS conduction times can be measured and processed to determine maximum, minimum and average RHP-LHS conduction times that are stored in memory, if that function is programmed ON.

Then, the process is repeated after a delay set forth in step S516 and if the criteria of steps S406–S414 continue to be satisfied to measure and store comparable LHP-RHS conduction times in steps S518–S530. Thus, the A-A or V-V pacing escape interval is reestablished in step S518 after a programmed number "N" of normal pacing mode escape intervals are counted in step S516, and the escape interval is timed out in step S520. An LHP pulse is delivered in step S524 to the LHC when the escape interval times out as determined in step S522. The RHC sense amplifier is enabled in step S526, typically after a blanking period, to detect the conducted depolarization that arrives at the RHC pace/sense electrodes in step S528. The LHP-RHS conduction time is measured and stored in step S530. Again, steps S518–S530 can be repeated via the broken line path so that a series of LHP-RHS conduction times can be measured and processed to determine maximum, minimum and average LHP-RHS conduction times that are stored in memory, if that function is programmed ON.

Conclusion

All patents and publications referenced herein are hereby incorporated by reference in their entireties.

It will be understood that certain of the above-described structures, functions and operations of the pacing systems of the preferred embodiments are not necessary to practice the present invention and are included in the description simply for completeness of an exemplary embodiment or embodiments. It will also be understood that there may be other structures, functions and operations ancillary to the typical operation of an AV synchronous, three or four chamber pacemaker that are not disclosed and are not necessary to the practice of the present invention.

In addition, it will be understood that specifically described structures, functions and operations set forth in the above-referenced patents can be practiced in conjunction with the present invention, but they are not essential to its practice. All such listed patents are incorporated herein by reference in their entireties. It is therefore to be understood, that within the scope of the appended claims, the invention may be practiced otherwise than as specifically described without actually departing from the spirit and scope of the present invention.

What is claimed is:

1. For use in a cardiac pacing system, a method comprising the steps of:
    (a) detecting a first ventricular event in a selected one of the first and second ventricular sites;
    (b) detecting a second ventricular depolarization in the other of the first and second ventricular sites;
    (c) measuring an elapsed conduction time from the first ventricular event to the second ventricular depolarization; and
    (d) utilizing the elapsed conduction time as an indicator of the state of heart failure and storing the elapsed conduction time in a storage device.

2. The method of claim 1, wherein the first ventricular event of step (a) is a ventricular depolarization.

3. The method of claim 1, and further including the step of repeating steps (a) through (d).

4. The method of claim 3, and further including the step of utilizing multiple measured elapsed conduction times to develop trend data representative of the state of heart failure.

5. The method of claim 1, and further including the steps of:
    timing an escape interval prior to step (a); and
    wherein the first ventricular event of step (a) is a first ventricular pace pulse delivered to the selected one of the first and second ventricular sites upon the expiration of the escape interval.

6. The method of claim 5, wherein the cardiac pacing system is capable of delivering a second ventricular pace pulse to the other of the first and second ventricular sites at a predetermined time relative to the first ventricular pace pulse and wherein step (b) includes the step of periodically suspending the delivery of the second ventricular pace pulse to detect the second ventricular depolarization.

7. A cardiac pacing system capable of delivering electrical stimulus to first and second ventricular sites, comprising:
    a timing circuit to begin measuring a time interval from a first ventricular event occurring at a selected one of the first and second ventricular sites;
    a sensing circuit coupled to the timing circuit to detect a second ventricular depolarization in the other of the first and second ventricular sites; and
    a storage device coupled to the timing circuit to store one or more elapsed conduction times, wherein the timing circuit is capable of measuring an elapsed conduction time from the first ventricular event to the second ventricular depolarization and wherein the elapsed conduction time may be utilized as an indicator of the state of heart failure.

8. The system of claim 7, and further including a processing circuit coupled to the timing circuit to utilize the elapsed conduction time as an indicator of the state of heart failure.

9. The system of claim 7, wherein the first ventricular event is a first ventricular depolarization, and further including a sensing circuit coupled to the timing circuit to sense the first ventricular event.

10. A cardiac pacing system capable of delivering electrical stimulus to first and second ventricular sites, comprising:
a timing circuit to be in measuring a time interval from a first ventricular event occurring at a selected one of the first and second ventricular sites;
a sensing circuit coupled to the timing circuit to detect a second ventricular depolarizatlon in the other of the first and second ventricular sites, wherein the timing circuit is capable of measuring an elapsed conduction time from the first ventricular event to the second ventricular depolarization and wherein the elapsed conduction time may be utilized as an indicator of the state of heart failure, wherein the first ventricular event is a first pacing pulse, and further including an output circuit coupled to the timing circuit to provide the first pacing pulse.

11. The system of claim 10, wherein the output circuit is capable of delivering a second pacing pulse to the other one of the first and second ventricular sites, and further including means for suspending the delivery of the second pacing pulse to allow the sensing circuit to detect the second ventricular depolarization.

12. The system of claim 7, and further including a processing circuit coupled to the timing circuit to develop trend data from the stored elapsed conduction times, the trend data being indicative of the state of heart failure.

13. A cardiac pacing system capable of delivering electrical stimulus to first and second ventricular sites, comprising:
a timing circuit to begin measuring a time interval from a first ventricular event occurring at a selected one of the first and second ventricular sites;
a sensing circuit coupled to the timing circuit to detect a second ventricular depolarization in the other of the first and second ventricular sites, wherein the timing circuit is capable of measuring an elapsed conduction time from the first ventricular event to the second ventricular depolarization and wherein the elapsed conduction time may be utilized as an indicator of the state of heart failure, and further including a communication circuit coupled to the timing circuit to transfer one or more elapsed conduction times to an external device.

14. In a multi-site, cardiac pacing system having memory for storing data and wherein ventricular pacing pulses are delivered to first and second ventricular sites synchronously within a V-V pace delay at a predetermined pacing rate in accordance with the steps of:
(a) timing a ventricular pacing escape interval of a heart cycle;
(b) detecting a ventricular depolarization in a selected one of the first and second ventricular sites within the pacing escape interval and, in response, terminating the pacing escape interval and providing a first ventricular sense (VS) event;
(c) delivering a first ventricular pace (VP) pulse to the selected one of the first and second ventricular sites upon the time-out of the pacing escape interval without provision of a first VS event;
(d) timing the V-V pace delay from a first VS event occurring prior to the time-out of the pacing escape interval or from a first VP pulse delivered upon time-out of the pacing escape interval; and
(e) delivering a second VP pulse to the other of the first and second ventricular sites upon the time-out of the V-V pace delay;

a method of periodically deriving trend data representative of the state of heart failure as evidenced by ventricular conduction time between the first and second ventricular sites comprising the steps of:
(f) detecting a ventricular depolarization in the other of the first and second ventricular sites during the one or more heart cycle and providing a second VS event in response;
(g) measuring one of an elapsed VS-VS conduction time from a first VS event to the second VS event or an elapsed VP-VS conduction time from the first VP pulse to the second VS event; and
(h) storing in memory the measured one of the elapsed VS-VS conduction time or the elapsed VP-VS conduction time,
whereby trend data representative of the state of heart failure as evidenced by changes in the stored one of the elapsed VS-VS conduction time or the elapsed VP-VS conduction time between the first and second ventricular sites is accumulated for analysis of the trend.

15. The method of claim 14, further comprising the step of suspending steps (d) and (e) while steps (a) through (c) and (f) through (h) are performed for one or more heart cycle.

16. The method of claim 15, wherein:
said first ventricular site is a right ventricular site in or adjacent to the right ventricle and said second ventricular site is a left ventricular site in or adjacent to the left ventricle; and
the first VS event signals are right VS event signals, and the second VS event signals are left VS event signals,
whereby spontaneous cardiac depolarizations of the right and left ventricles are sensed and VP pulses are delivered to the right and left heart ventricles during steps (a) through (e) for improving the hemodynamic efficiency of a sick heart suffering from conduction times in conducting spontaneous or evoked depolarizations through the right and left ventricles that compromise cardiac output.

17. The method of claim 15, wherein:
said first ventricular site is a left ventricular site in or adjacent to the left ventricle and said second ventricular site is a right ventricular site in or adjacent to the right ventricle; and
the first VS event signals are left VS event signals, and the second VS event signals are right VS event signals,
whereby spontaneous cardiac depolarizations of the right and left ventricles are sensed and VP pulses are delivered to the right and left heart ventricles during steps (a) through (e) for improving the hemodynamic efficiency of a sick heart suffering from conduction times in conducting spontaneous or evoked depolarizations through the right and left ventricles that compromise cardiac output.

18. The method of claim 15, further comprising:
repeating steps (a)–(c) and (f)–(h) to derive a plurality of measured ones of the elapsed VS-VS conduction time or the elapsed VP-VS conduction time; and
determining one or more of the longest, shortest, and average elapsed VS-VS conduction time or VP-VS conduction time; and wherein:
step (h) further comprises storing the determined one or more of the longest, shortest, and average elapsed VS-VS conduction time or VP-VS conduction time.

19. The method of claim 15, wherein step (h) further comprises storing one or more related data including a date and time stamp of the measurement event, the prevailing heart rate, and an activity level of the patient or other indicator of physiologic need for cardiac output.

20. The method of claim 14, wherein:
step (c) further comprises selectively delivering a first VP pulse to the selected one of the first and second ventricular sites upon provision of the first VS event during time-out of the pacing escape interval as a VS/VP pulse;
step (d) further comprises timing the V-V pace delay from the first VP pulse delivered upon time-out of the pacing escape interval or selectively either from the VS/VP pulse delivered synchronously with the first VS event or from the first VS event occurring prior to the time-out of the pacing escape interval;
step (g) further comprises measuring one of the elapsed VP-VS conduction time from the first VP pulse delivered at the end of the pacing escape interval or the elapsed VS/VP-VS conduction time from the first VP pulse delivered upon a first VS event occurring during the time-out of the pacing escape interval or the VS-VS conduction time; and
step (h) further comprises storing in memory the measured one of the VP-VS conduction time, the VS/VP-VP conduction time or the VS-VS conduction time, whereby trend data representative of the state of heart failure as evidenced by changes in the stored one of the elapsed VS-VS conduction time, the VP-VS conduction time, and the VS/VP-VS conduction time between the first and second ventricular sites is accumulated for analysis of the trend.

21. The method of claim 14, wherein:
said first ventricular site is a right ventricular site in or adjacent to the right ventricle and said second ventricular site is a left ventricular site in or adjacent to the left ventricle; and
the first VS event signals are right VS event signals, and the second VS event signals are left VS event signals, whereby spontaneous cardiac depolarizations of the right and left ventricles are sensed and VP pulses are delivered to the right and left heart ventricles during steps (a) through (e) for improving the hemodynamic efficiency of a sick heart suffering from conduction times in conducting spontaneous or evoked depolarizations through the right and left ventricles that compromise cardiac output.

22. The method of claim 14, wherein:
said first ventricular site is a left ventricular site in or adjacent to the left ventricle and said second ventricular site is a right ventricular site in or adjacent to the right ventricle; and
the first VS event signals are left VS event signals, and the second VS event signals are right VS event signals, whereby spontaneous cardiac depolarizations of the right and left ventricles are sensed and VP pulses are delivered to the right and left heart ventricles during steps (a) through (e) for improving the hemodynamic efficiency of a sick heart suffering from conduction times in conducting spontaneous or evoked depolarizations through the right and left ventricles that compromise cardiac output.

23. The method of claim 14, further comprising:
repeating steps (a)–(c) and (f)–(h) to derive a plurality of measured ones of the elapsed VS-VS conduction time or the elapsed VP-VS conduction time; and determining one or more of the longest, shortest, and average elapsed VS-VS conduction time or VP-VS conduction time; and wherein:
step (h) further comprises storing the determined one or more of the longest, shortest, and average elapsed VS-VS conduction time or VP-VS conduction time.

24. The method of claim 14, wherein step (h) further comprises storing one or more related data including a date and time stamp of the measurement event, the prevailing heart rate, and an activity level of the patient or other indicator of physiologic need for cardiac output.

25. The method of claim 14, wherein:
step (c) further comprises selectively delivering a first VP pulse to the selected one of the first and second ventricular sites upon provision of the first VS event during time-out of the pacing escape interval as a VS/VP pulse;
step (d) further comprises timing the V-V pace delay from the first VP pulse delivered upon time-out of the pacing escape interval or selectively either from the VS/VP pulse delivered synchronously with the first VS event or from the first VS event occurring prior to the time-out of the pacing escape interval;
step (g) further comprises measuring one of the elapsed VP-VS conduction time from the first VP pulse delivered at the end of the pacing escape interval or the elapsed VS/VP-VS conduction time from the first VP pulse delivered upon a first VS event occurring during the time-out of the pacing escape interval or the VS-VS conduction time; and
step (h) further comprises storing in memory the measured one of the VP-VS conduction time, the VS/VP-VP conduction time or the VS-VS conduction time, whereby trend data representative of the state of heart failure as evidenced by changes in the stored one of the elapsed VS-VS conduction time, the VP-VS conduction time, and the VS/VP-VS conduction time between the first and second ventricular sites is accumulated for analysis of the trend.

26. In a multi-site, cardiac pacing system having memory for storing data and wherein ventricular pacing pulses are delivered to first and second ventricular sites synchronously within a V-V pace delay at a predetermined pacing rate by:
pacing escape interval timing means for timing a ventricular pacing escape interval of a heart cycle;
first ventricular sense event means for detecting a ventricular depolarization in a selected one of the first and second ventricular sites within the pacing escape interval and, in response, terminating the pacing escape interval and providing a first ventricular sense (VS) event;
first ventricular pace means for delivering a first ventricular pace (VP) pulse to the selected one of the first and second ventricular sites upon the time-out of the pacing escape interval without provision of a first VS event;
pace delay timing means for timing the V-V pace delay from a first VS event occurring prior to the time-out of the pacing escape interval or from a first VP pulse delivered upon time-out of the pacing escape interval; and
second ventricular pace means for delivering a second VP pulse to the other of the first and second ventricular sites upon the time-out of the V-V pace delay;
apparatus for periodically deriving trend data representative of the state of heart failure as evidenced by ventricular conduction time between the first and second ventricular sites comprising:

suspending means for suspending the pace delay timing means for one or more heart cycle;

second ventricular sense event means for detecting a ventricular depolarization in the other of the first and second ventricular sites during the one or more heart cycle following a first VS event or a first VP pulse and providing a second VS event in response;

conduction time measuring means for measuring one of an elapsed VS-VS conduction time from a first VS event to the second VS event or an elapsed VP-VS conduction time from the first VP pulse to the second VS event; and storing means for storing in memory the measured one of the elapsed VS-VS conduction time or the elapsed VP-VS conduction time, whereby trend data representative of the state of heart failure as evidenced by changes in the stored one of the elapsed VS-VS conduction time or the elapsed VP-VS conduction time between the first and second ventricular sites is accumulated for analysis of the trend.

27. The system of claim 26, wherein the apparatus for periodically deriving trend data representative of the state of heart failure as evidenced by ventricular conduction time between the first and second ventricular sites further comprises suspending means for suspending the pace delay timing means for one or more heart cycles.

28. The system of claim 27, wherein:

said first ventricular site is a right ventricular site in or adjacent to the right ventricle and said second ventricular site is a left ventricular site in or adjacent to the left ventricle; and the first VS event signals are right VS event signals, and the second VS event signals are left VS event signals, whereby spontaneous cardiac depolarizations of the right and left ventricles are sensed and VP pulses are delivered to the right and left heart ventricles during steps (a) through (e) for improving the hemodynamic efficiency of a sick heart suffering from conduction times in conducting spontaneous or evoked depolarizations through the right and left ventricles that compromise cardiac output.

29. The system of claim 27, wherein:

said first ventricular site is a left ventricular site in or adjacent to the left ventricle and said second ventricular site is a right ventricular site in or adjacent to the right ventricle; and the first VS event signals are left VS event signals, and the second VS event signals are right VS event signals, whereby spontaneous cardiac depolarizations of the right and left ventricles are sensed and VP pulses are delivered to the right and left heart ventricles during steps (a) through (e) for improving the hemodynamic efficiency of a sick heart suffering from conduction times in conducting spontaneous or evoked depolarizations through the right and left ventricles that compromise cardiac output.

30. The system of claim 27, wherein:

the suspending means is operable over a plurality of heart cycles; and the conduction time measuring means measures a plurality of measured ones of the elapsed VS-VS conduction time or the elapsed VP-VS conduction time and further comprising:

means for determining one or more of the longest, shortest, and average elapsed VS-VS conduction time or VP-VS conduction time; and wherein:

the storing means stores the determined one or more of the longest, shortest, and average elapsed VS-VS conduction time or VP-VS conduction time.

31. The system of claim 27, wherein the storing means further comprises means for storing one or more related data including a date and time stamp of the measurement event, the prevailing heart rate, and an activity level of the patient or other indicator of physiologic need for cardiac output.

32. The system of claim 27, wherein the first ventricular pace means is selectively operable for delivering a first VP pulse to the selected one of the first and second ventricular sites upon provision of the first VS event during time-out of the pacing escape interval as a VS/VP pulse;

the pace delay timing means includes means for timing the V-V pace delay from the first VP pulse delivered upon time-out of the pacing escape interval or selectively either from the VS/VP pulse delivered synchronously with the first VS event or from the first VS event occurring prior to the time-out of the pacing escape interval;

the conduction time measuring means includes means for measuring one of the elapsed VP-VS conduction time from the first VP pulse delivered at the end of the pacing escape interval or the elapsed VS/VP-VS conduction time from the first VP pulse delivered upon a first VS event occurring during the time-out of the pacing escape interval or the VS-VS conduction time; and the storing means includes means for storing in memory the measured one of the VP-VS conduction time, the VS/VP-VP conduction time or the VS-VS conduction time, whereby trend data representative of the state of heart failure as evidenced by changes in the stored one of the elapsed VS-VS conduction time, the VP-VS conduction time, and the VS/VP-VS conduction time between the first and second ventricular sites is accumulated for analysis of the trend.

33. The system of claim 26, wherein:

said first ventricular site is a right ventricular site in or adjacent to the right ventricle and said second ventricular site is a left ventricular site in or adjacent to the left ventricle; and the first VS event signals are right VS event signals, and the second VS event signals are left VS event signals, whereby spontaneous cardiac depolarizations of the right and left ventricles are sensed and VP pulses are delivered to the right and left heart ventricles during steps (a) through (e) for improving the hemodynamic efficiency of a sick heart suffering from conduction times in conducting spontaneous or evoked depolarizations through the right and left ventricles that compromise cardiac output.

34. The system of claim 26, wherein:

said first ventricular site is a left ventricular site in or adjacent to the left ventricle and said second ventricular site is a right ventricular site in or adjacent to the right ventricle; and the first VS event signals are left VS event signals, and the second VS event signals are right VS event signals, whereby spontaneous cardiac depolarizations of the right and left ventricles are sensed and VP pulses are delivered to the right and left heart ventricles during steps (a) through (e) for improving the hemodynamic efficiency of a sick heart suffering from conduction times in conducting spontaneous or evoked depolarizations through the right and left ventricles that compromise cardiac output.

35. The system of claim 26, wherein the conduction time measuring means measures a plurality of measured ones of the elapsed VS-VS conduction time or the elapsed VP-VS conduction time and further comprising:

means for determining one or more of the longest, shortest, and average elapsed VS-VS conduction time or VP-VS conduction time; and wherein:

the storing means stores the determined one or more of the longest, shortest, and average elapsed VS-VS conduction time or VP-VS conduction time.

36. The system of claim 26, wherein the storing means further comprises means for storing one or more related data including a date and time stamp of the measurement event, the prevailing heart rate, and an activity level of the patient or other indicator of physiologic need for cardiac output.

37. The system of claim 26, wherein the first ventricular pace means is selectively operable for delivering a first VP pulse to the selected one of the first and second ventricular sites upon provision of the first VS event during time-out of the pacing escape interval as a VS/VP pulse;

the pace delay timing means times the V-V pace delay from the first VP pulse delivered upon time-out of the pacing escape interval or selectively either from the VS/VP pulse delivered synchronously with the first VS event or from the first VS event occurring prior to the time-out of the pacing escape interval;

the conduction time measuring means measures one of the elapsed VP-VS conduction time from the first VP pulse delivered at the end of the pacing escape interval or the elapsed VS/VP-VS conduction time from the first VP pulse delivered upon a first VS event occurring during the time-out of the pacing escape interval or the VS-VS conduction time; and the storing means stores in memory the measured one of the VP-VS conduction time, the VS/VP-VP conduction time or the VS-VS conduction time, whereby trend data representative of the state of heart failure as evidenced by changes in the stored one of the elapsed VS-VS conduction time, the VP-VS conduction time, and the VS/VP-VS conduction time between the first and second ventricular sites is accumulated for analysis of the trend.

38. In a multi-site, AV sequential, cardiac pacing system having memory for storing data and wherein ventricular pacing pulses are delivered to the right and left ventricles synchronously within a V-V pace delay following time-out of an AV delay from a preceding delivered atrial pace pulse or an atrial sense event in accordance with the steps of:

(a) timing an AV delay from a preceding delivered atrial pace pulse or an atrial sense event;

(b) detecting a ventricular depolarization in a selected one of the right and left ventricle within the AV delay and, in response, terminating the AV delay and providing a first ventricular sense (VS) event;

(c) delivering a first ventricular pace (VP) pulse to the selected one of the right and left ventricle upon either the time-out of the AV delay without provision of a first VS event or upon provision of the first VS event during time-out of the AV delay;

(d) timing the V-V pace delay from a first VS event occurring prior to the time-out of the AV delay or from a first VP pulse delivered either upon provision of the first VS event or upon time-out of the AV delay; and (e) delivering a second VP pulse to the other of the right and left ventricle upon the time-out of the V-V pace delay;

a method of periodically deriving trend data representative of the state of heart failure as evidenced by ventricular conduction time between the right and left ventricle comprising the steps of:

(f) suspending steps (d) and (e) while steps (a) through (c) are performed for one or more heart cycle;

(g) detecting a ventricular depolarization in the other of the right and left ventricle during the one or more heart cycle and providing a second VS event in response;

(h) measuring one of the elapsed VS-VS conduction time from a first VS event or the elapsed VP-VS conduction time from the first VP pulse delivered at the end of the AV delay or the elapsed VS/VP-VS conduction time from the first VP pulse delivered upon a first VS event occurring during the time-out of the AV delay; and (i) storing in memory the measured one of the elapsed VS-VS conduction time or the elapsed VP-VS conduction time or the elapsed VS/VP-VS conduction time whereby trend data representative of the state of heart failure as evidenced by changes in the stored one of the elapsed VS-VS conduction time, the VP-VS conduction time, and the VS/VP-VS conduction time between the right and left ventricles is accumulated for analysis of the trend.

39. The method of claim 38, further comprising:

repeating steps (a)–(c) and (f)–(h) to derive a plurality of measured ones of the elapsed VS-VS conduction time or the VS/VP-VS conduction time or the elapsed VP-VS conduction time; and determining one or more of the longest, shortest, and average elapsed VS-VS conduction time or VS/VP-VS conduction time or VP-VS conduction time; and wherein:

step (i) further comprises storing the determined one or more of the longest, shortest, and average elapsed VS-VS conduction time or VS/VP-VS conduction time or VP-VS conduction time.

40. In a multi-site, AV sequential, cardiac pacing system having memory for storing data and wherein ventricular pacing pulses are delivered to the right and left ventricles synchronously within a V-V pace delay following time-out of an AV delay from a preceding delivered atrial pace pulse or an atrial sense event by:

(a) means for timing an AV delay from a preceding delivered atrial pace pulse or an atrial sense event;

(b) means for detecting a ventricular depolarization in a selected one of the right and left ventricle within the AV delay and, in response, terminating the AV delay and providing a first ventricular sense (VS) event;

(c) means for delivering a first ventricular pace (VP) pulse to the selected one of the right and left ventricle upon either the time-out of the AV delay without provision of a first VS event or upon provision of the first VS event during time-out of the AV delay;

(d) means for timing the V-V pace delay from a first VS event occurring prior to the time-out of the AV delay or from a first VP pulse delivered either upon provision of the first VS event or upon time-out of the AV delay; and (e) means for delivering a second VP pulse to the other of the right and left ventricle upon the time-out of the V-V pace delay;

apparatus for periodically deriving trend data representative of the state of heart failure as evidenced by ventricular conduction time between the right and left ventricle comprising:

(f) means for suspending means (d) and (e) while means (a) through (c) operate for one or more heart cycle;

(g) means for detecting a ventricular depolarization in the other of the right and left ventricle during the one or more heart cycle and providing a second VS event in response; and (h) means for measuring and storing in memory one of the elapsed VS-VS conduction time from a first VS event or the elapsed VP-VS conduction time from the first VP pulse delivered at the end of the AV delay or the elapsed VS/VP-VS conduction time from the first VP pulse delivered upon a first VS event occurring during the time-out of the AV delay, whereby trend data representative of the state of heart failure as evidenced by changes in the stored one of the elapsed VS-VS conduction time, the VP-VS conduction time, and the VS/VP/VS conduction time between the right and left ventricles is accumulated for analysis of the trend.

41. The system of claim 40, wherein the conduction time measuring means measures a plurality of measured ones of the elapsed VS-VS conduction time or the elapsed VP-VS conduction time or the VS/VP-VS conduction time and further comprising:

means for determining one or more of the longest, shortest, and average the elapsed VS-VS conduction time or the VS/VP-VS conduction time or the elapsed VP-VS conduction time; and wherein:

the storing means stores the determined one or more of the longest, shortest, and average elapsed VS-VS conduction time or VP-VS conduction time or VS/VP-VS conduction time.

42. In a multi-site, cardiac pacing system having memory for storing data and wherein ventricular pacing pulses are delivered to first and second ventricular sites synchronously within a V-V pace delay at a predetermined pacing rate for improving the hemodynamic efficiency of a sick heart, a method of obtaining conduction time data comprising the steps of:

sensing spontaneous atrial depolarizations and providing atrial sense event signals;

timing out an AV delay from the atrial sense event signals;

sensing spontaneous cardiac depolarizations at a first ventricular site and providing first ventricular sense (VS) event signals;

sensing spontaneous cardiac depolarizations at a second ventricular site and providing second ventricular sense (VS) event signals;

upon time-out of the AV delay, delivering a first ventricular pace (VP) pulse to a predetermined one of the first and second ventricular sites;

measuring a VP-VS conduction time from a VP pulse delivered to the predetermined one of the first and second ventricular sites until the sensing of a cardiac depolarization at the other one of the first and second ventricular sites as a VS event signal; and storing in memory the VP-VS conduction time whereby trend data representative of the state of heart failure as evidenced by changes in the stored VP-VS conduction time between the first and second ventricular sites is accumulated for analysis of the trend.

43. The method of claim 42, wherein the first ventricular site is a right ventricular site and the second ventricular site is a left ventricular site and wherein:

the step of delivering a ventricular pace pulse to a predetermined one of the first and second ventricular sites upon provision of a first or second ventricular sense event signal during the timing out of the AV delay further comprises delivering a first VP pulse either as a right VP pulse to the right ventricular site to evoke a right ventricular depolarization or as a left VP pulse to the left ventricular site to evoke a left ventricular depolarization.

44. The method of claim 42, further comprising the steps of:

upon provision of a first or second ventricular sense event signal during the timing out of the AV delay, delivering a first VP pulse to the predetermined one of the first and second ventricular sites without delay as a VS/VP pulse;

measuring a VS/VP-VS conduction time from the VS/VP pulse until the sensing of a cardiac depolarization at the other one of the first and second ventricular sites as a VS event signal; and storing in memory the VS/VP-VS conduction time whereby trend data representative of the state of heart failure as evidenced by changes in the stored VP-VS conduction time between the first and second ventricular sites is accumulated for analysis of the trend.

45. The method of claim 42, further comprising the steps of:

measuring a VS-VS conduction time from the VS event signal at the first or second ventricular site during the time-out of the AV delay until the second VS event signal at the other one of the first and second ventricular sites; and storing in memory the VS-VS conduction time whereby trend data representative of the state of heart failure as evidenced by changes in the stored V-V conduction time between the first and second ventricular sites is accumulated for analysis of the trend.

46. The method of claim 42, further comprising the steps of:

delivering a first VP pulse to a selected one of the first and second ventricle upon either the time-out of the AV delay without provision of a first VS event or upon provision of the first VS event during time-out of the AV delay;

timing a V-V pace delay from a first VS event occurring prior to the time-out of the AV delay or from a first VP pulse delivered either upon provision of the first VS event or upon time-out of the AV delay; and delivering a second VP pulse to the other of the right and left ventricle upon the time-out of the V-V pace delay.

47. A multi-site cardiac pacing system for selectively sensing spontaneous ventricular cardiac depolarizations at spaced apart ventricular sites and delivering pace pulses to the spaced apart ventricular sites for improving the hemodynamic efficiency of a sick heart and having memory for storing data, wherein said pacing system further comprises:

an atrial pace/sense lead adapted to be advanced into relation with an atrial chamber to situate an atrial pace/sense electrode in or adjacent to the atrial chamber;

ventricular pace/sense lead means for situating a first ventricular pace/sense electrode at a first ventricular site and a second ventricular pace/sense electrode at a second ventricular site spaced from said first ventricular site; and a pace pulse generator coupled to said atrial pace/sense lead and said ventricular pace/sense lead means comprising:

an atrial sense amplifier coupled to said atrial pace/sense electrode for sensing spontaneous atrial depolarizations and providing atrial sense (AS) event signals;

an AV delay timer for timing out an AV delay from the AS event signals;

a first ventricular sense amplifier coupled to said first ventricular pace/sense electrode for sensing spontaneous cardiac depolarizations at the first ventricular site and providing first ventricular sense (VS) event signals;

a second ventricular sense amplifier coupled to said second ventricular electrode for sensing spontaneous cardiac depolarizations at the second ventricular site and providing second ventricular sense (VS) event signals;

an escape interval timer for timing out a V-A escape interval establishing a pacing rate from one of the first and second VS event signals occurring during the time-out of the AV delay or the V-A escape interval;

means for measuring a VP-VS conduction time from a VP pulse delivered to the predetermined one of the first and second ventricular sites until a VS event resulting from sensing of a cardiac depolarization at the other one of the first and second ventricular sites; and means for storing the VP-VS conduction time in memory whereby trend data representative of the state of heart failure as evidenced by changes in the stored VP-VS conduction time between the first and second ventricular sites is accumulated for analysis of the trend.

48. The system of claim 47, wherein the pulse generator further comprises:

ventricular trigger pacing means coupled to said ventricular pace/sense lead means and operable in response to provision of a first or second VS event signal during the time-out of the AV delay for delivering a VP pulse to a predetermined one of said first and second pace/sense electrodes at said first and second ventricular sites without delay; and V-A escape interval restarting means operable in response to provision of a first or second VS event signal during the time-out of the V-A escape interval for terminating and restarting the V-A escape interval, whereby triggered ventricular pacing is provided to at least one of the first and second ventricular sites only when a first or second VS event signal is provided during time-out of the AV delay.

49. The system of claim 48, wherein the first ventricular site is a right ventricular site and the second ventricular site is a left ventricular site.

50. The system of claim 47, wherein the pulse generator further comprises:

means operable upon provision of a first or second ventricular sense event signal during the timing out of the AV delay, delivering a first VP pulse to the predetermined one of the first and second ventricular sites without delay as a VS/VP pulse;

means for measuring a VS/VP-VS conduction time from the VS/VP pulse until the sensing of a cardiac depolarization at the other one of the first and second ventricular sites as a VS event signal; and means for storing the VS/VP-VS conduction time in memory whereby trend data representative of the state of heart failure as evidenced by changes in the stored VP-VS conduction time between the first and second ventricular sites is accumulated for analysis of the trend.

51. The system of claim 47, wherein the pulse generator further comprises:

means for measuring a VS-VS conduction time from the VS event signal at the first or second ventricular site until the second VS event signal at the other one of the first and second ventricular sites; and means for storing the VS-VS conduction time in memory whereby trend data representative of the state of heart failure as evidenced by changes in the stored V-V conduction time between the first and second ventricular sites is accumulated for analysis of the trend.

52. The system of claim 47, wherein the pulse generator further comprises:

means for delivering a first VP pulse to the selected one of the right and left ventricle upon either the time-out of the AV delay without provision of a first VS event or upon provision of the first VS event during time-out of the AV delay;

means for timing a V-V pace delay from a first VS event occurring prior to the time-out of the AV delay or from a first VP pulse delivered either upon provision of the first VS event or upon time-out of the AV delay; and means for delivering a second VP pulse to the other of the right and left ventricle upon the time-out of the V-V pace delay.

53. In a multi-site, cardiac pacing system having memory for storing data and having the capability of sensing cardiac depolarizations in a right heart chamber (RHC) to develop an RHC sense (RHS) event signal and a left heart chamber (LHC) to develop an LHC sense (LHS) event signal and to selectively pace in the RHC and LHC whereby RHC pace (RHP) pulses are selectively delivered to the RHC and LHC pace (LHP) pulses are delivered to the LHC synchronously within an RHP-LHP delay at a predetermined pacing rate for improving the hemodynamic efficiency of a sick heart, a method of measuring the conduction time between the RHC and the LHC comprising the steps of:

timing out a pacing escape interval;

upon time-out of the pacing escape interval, delivering one of an RHP pulse to the RHC or an LHP pulse to the LHC;

after delivery of an RHP pulse, sensing an LHS event signal in the LHC;

after delivery of an LHP pulse, sensing an RHS event signal in the RHC;

measuring an RHP-LHS conduction time from an RHP pulse delivered to the RHC to the sensing of an LHS event in the LHC;

measuring an LHP-RHS conduction time from an LHP pulse delivered to the LHC to the sensing of an RHS event in the RHC;

storing in memory one of the RHP-LHS conduction time or the LHP-RHS conduction time, whereby trend data representative of the state of heart failure as evidenced by changes in the stored RHP-LHS conduction time or the LHP-RHS conduction time is accumulated for analysis of the trend.

54. The method of claim 53, wherein the RHC is the right atrium and the LHC is the left atrium.

55. The method of claim 53, wherein the RHC is the right ventricle and the LHC is the left ventricle.

56. In a multi-site, cardiac pacing system having memory for storing data and having the capability of sensing cardiac depolarizations in a right heart chamber (RHC) to develop an RHC sense (RHS) event signal and a left heart chamber (LHC) to develop an LHC sense (LHS) event signal and to selectively pace in the RHC and LHC whereby RHC pace (RHP) pulses are selectively delivered to the RHC and LHC pace (LHP) pulses are delivered to the LHC synchronously within an RHP-LHP delay at a predetermined pacing rate for improving the hemodynamic efficiency of a sick heart, a method of measuring the conduction time between the RHC and the LHC comprising the steps of:

timing out a pacing escape interval;

upon time-out of the pacing escape interval, delivering an RHP pulse to the RHC;

after delivery of the RHP pulse, sensing an LHS event signal in the LHC;

measuring an RHP-LHS conduction time from an RHP pulse delivered to the RHC to the sensing of an LHS event in the LHC;

storing the RHP-LHS conduction time in memory;

restarting the pacing escape interval;

upon time-out of the pacing escape interval, delivering an LHP pulse to the LHC;

after delivery of the LHP pulse, sensing an RHS event signal in the RHC;

measuring an LHP-RHS conduction time from an LHP pulse delivered to the LHC to the sensing of an RHS event in the RHC; and storing the LHP-RHS conduction time in memory, whereby trend data representative of the state of heart failure as evidenced by changes in the stored RHP-LHS conduction time and the LHP-RHS conduction time is accumulated for analysis of the trend.

57. The method of claim 56, wherein the RHC is the right atrium and the LHC is the left atrium.

58. The method of claim 56, wherein the RHC is the right ventricle and the LHC is the left ventricle.

59. The method of claim 56, further comprising the step of retrieving the trend data comprising the RHP-LHS conduction time and the LHP-RHS conduction time and comparing the stored RHP-LHS conduction times with the LHP-RHS conduction times.

60. In a multi-site, cardiac pacing system having memory for storing data and having the capability of sensing cardiac depolarizations in a right heart chamber (RHC) to develop an RHC sense (RHS) event signal and a left heart chamber (LHC) to develop an LHC sense (LHS) event signal and to selectively pace in the RHC and LHC whereby RHC pace (RHP) pulses are selectively delivered to the RHC and LHC pace (LHP) pulses are delivered to the LHC synchronously within an RHP-LHP delay at a predetermined pacing rate for improving the hemodynamic efficiency of a sick heart, apparatus for measuring the conduction time between the RHC and the LHC comprising:

means for timing out a pacing escape interval;

upon time-out of the pacing escape interval, delivering one of an RHP pulse to the RHC or an LHP pulse to the LHC;

means for sensing an LHS event signal in the LHC after delivery of an RHP pulse;

means for sensing an RHS event signal in the RHC after delivery of an LHP pulse;

means for measuring an RHP-LHS conduction time from an RHP pulse delivered to the RHC to the sensing of an LHS event in the LHC;

means for measuring an LHP-RHS conduction time from an LHP pulse delivered to the LHC to the sensing of an RHS event in the RHC;

means for storing in memory one of the RHP-LHS conduction time or the LHP-RHS conduction time, whereby trend data representative of the state of heart failure as evidenced by changes in the stored RHP-LHS conduction time or the LHP-RHS conduction time is accumulated for analysis of the trend.

61. The system of claim 60, wherein the RHC is the right atrium and the LHC is the left atrium.

62. The system of claim 60, wherein the RHC is the right ventricle and the LHC is the left ventricle.

63. In a multi-site, cardiac pacing system having memory for storing data and having the capability of sensing cardiac depolarizations in a right heart chamber (RHC) to develop an RHC sense (RHS) event signal and a left heart chamber (LHC) to develop an LHC sense (LHS) event signal and to selectively pace in the RHC and LHC whereby RHC pace (RHP) pulses are selectively delivered to the RHC and LHC pace (LHP) pulses are delivered to the LHC synchronously within an RHP-LHP delay at a predetermined pacing rate for improving the hemodynamic efficiency of a sick heart, apparatus for measuring the conduction time between the RHC and the LHC comprising:

means for timing out a pacing escape interval;

means for delivering an RHP pulse to the RHC upon time-out of the pacing escape interval;

means for sensing an LHS event signal in the LHC after delivery of the RHP pulse;

means for measuring an RHP-LHS conduction time from an RHP pulse delivered to the RHC to the sensing of an LHS event in the LHC;

means for storing the RHP-LHS conduction time in memory;

means for restarting the pacing escape interval;

means for delivering an LHP pulse to the LHC upon time-out of the pacing escape interval;

means for sensing an RHS event signal in the RHC after delivery of the LHP pulse;

means for measuring an LHP-RHS conduction time from an LHP pulse delivered to the LHC to the sensing of an RHS event in the RHC; and means for storing the LHP-RHS conduction time in memory, whereby trend data representative of the state of heart failure as evidenced by changes in the stored RHP-LHS conduction time and the LHP-RHS conduction time is accumulated for analysis of the trend.

64. The system of claim 63, wherein the RHC is the right atrium and the LHC is the left atrium.

65. The system of claim 63, wherein the RHC is the right ventricle and the LHC is the left ventricle.

* * * * *